(12) United States Patent
Stochniol et al.

(10) Patent No.: US 8,524,945 B2
(45) Date of Patent: Sep. 3, 2013

(54) METHOD FOR PRODUCING ACROLEIN COMPRISING THE REGENERATION OF A RAW GLYCERIN PHASE

(75) Inventors: Guido Stochniol, Haltern am See (DE); Goetz Baumgarten, Haltern am See (DE); Franz-Felix Kuppinger, Marl (DE)

(73) Assignee: Evonik Degussa GmbH, Essen (DE)

( * ) Notice: Subject to any disclaimer, the term of this patent is extended or adjusted under 35 U.S.C. 154(b) by 18 days.

(21) Appl. No.: 13/128,538

(22) PCT Filed: Nov. 3, 2009

(86) PCT No.: PCT/EP2009/064500
§ 371 (c)(1),
(2), (4) Date: Jul. 1, 2011

(87) PCT Pub. No.: WO2010/066513
PCT Pub. Date: Jun. 17, 2010

(65) Prior Publication Data
US 2011/0275777 A1 Nov. 10, 2011

(30) Foreign Application Priority Data
Dec. 9, 2008 (DE) .......................... 10 2008 060 888

(51) Int. Cl.
*C07C 51/00* (2006.01)
*C07C 31/22* (2006.01)

(52) U.S. Cl.
USPC ......................................... 562/599; 568/869

(58) Field of Classification Search
USPC .......... 568/869; 562/599; 526/75; 422/131, 422/610, 617, 620
See application file for complete search history.

(56) References Cited

U.S. PATENT DOCUMENTS 5,250,182 A  10/1993  Bento et al.
5,387,720 A * 2/1995  Neher et al. ................. 568/486
(Continued)

FOREIGN PATENT DOCUMENTS

DE    4238493 C1    4/1994
DE    4328407 C1    9/1994
(Continued)

OTHER PUBLICATIONS

Pagliaro et al. "The Future of Glycerol: New Uses of a Versatile Raw Material," RSC, Cambridge (UK), 2008, Chapter 1; published on Apr. 3, 2008 on http://pubs.rsc.org.*

(Continued)

*Primary Examiner* — Vu A Nguyen
(74) *Attorney, Agent, or Firm* — Philip P. McCann; John P. Zimmer; Smith Moore Leatherwood LLP

(57) ABSTRACT

The invention relates to a method for producing acrolein by dehydrating an aqueous glycerin phase in an acrolein reaction region, obtaining an aqueous acrolein reaction phase; at least partially separating the aqueous acrolein reaction phase into an acrolein-rich acrolein phase and an acrolein-poor residual phase comprising glycerin, water and various other residuals; and recirculating at least part of the residual phase into the acrolein reaction region. Additionally, removing at least one of the residuals, other than glycerin or water, from either of the glycerin phase or a mixture phase obtained by mixing the glycerol phase with the low-acrolein residue phase and feeding the resulting purified glycerin or mixture phase into the acrolein reaction region. The invention furthermore relates to a method for producing acrylic acid, water-absorbing polymer formations, compounds and hygiene articles, and to devices for carrying out those methods.

11 Claims, 9 Drawing Sheets

(56) References Cited

U.S. PATENT DOCUMENTS

| | | | |
|---|---|---|---|
| 5,562,827 | A | 10/1996 | Schmidt et al. |
| 6,639,108 | B2 | 10/2003 | Schiffer et al. |
| 6,764,671 | B2 | 7/2004 | Haas et al. |
| 6,838,572 | B2 | 1/2005 | Haas et al. |
| 6,878,836 | B2 | 4/2005 | Haas et al. |
| 7,002,050 | B2 | 2/2006 | Santiago et al. |
| 7,005,528 | B2 | 2/2006 | Haas et al. |
| 7,141,683 | B2 | 11/2006 | Haas et al. |
| 7,169,945 | B2 | 1/2007 | Haas et al. |
| 7,179,875 | B2 | 2/2007 | Fuchs et al. |
| 7,722,847 | B2 | 5/2010 | Haas et al. |
| 7,846,861 | B2 | 12/2010 | Redlingshofer et al. |
| 2004/0028589 | A1 | 2/2004 | Reisinger et al. |
| 2004/0029718 | A1 | 2/2004 | Sakuth et al. |
| 2005/0242031 | A1 | 11/2005 | Reusch et al. |
| 2006/0276334 | A1 | 12/2006 | Balduf et al. |
| 2008/0119663 | A1* | 5/2008 | Redlingshoefer et al. .... 554/148 |
| 2008/0251456 | A1 | 10/2008 | Wiese et al. |
| 2009/0023006 | A1 | 1/2009 | Bub et al. |
| 2009/0032465 | A1 | 2/2009 | Baumgarten et al. |
| 2009/0068440 | A1* | 3/2009 | Bub et al. ................. 428/327 |

FOREIGN PATENT DOCUMENTS

| | | |
|---|---|---|
| DE | 10138150 A1 | 2/2003 |
| DE | 102005028624 A1 | 12/2006 |
| DE | 102007004350 A1 | 7/2008 |
| DE | 102007019379 A1 | 10/2008 |
| EP | 0959062 A1 | 11/1999 |
| WO | 03051809 A1 | 6/2003 |
| WO | 2006074249 A1 | 7/2006 |
| WO | 2006074259 A2 | 7/2006 |
| WO | 2006092272 A2 | 9/2006 |
| WO | 2008023040 A2 | 2/2008 |

OTHER PUBLICATIONS

Bub et al., U.S. Appl. No. 13/029,208, filed Feb. 17, 2011.
German language International Search Report, mailed on Jun. 1, 2010 in PCT/EP2009/064500.
German language Written Opinion, mailed on Jun. 1, 2010 in PCT/EP2009/064500.
International Search Report, mailed on Jun. 1, 2010 in PCT/EP2009/064500.
Kuppinger et al., U.S. Appl. No. 12/438,295, filed Nov. 12, 2009.
Zanthoff et al., U.S. Appl. No. 13/060,599, filed Mar. 28, 2011.

* cited by examiner

METHOD FOR PRODUCING ACROLEIN COMPRISING THE REGENERATION OF A RAW GLYCERIN PHASE

This application is a national stage application under 35 U.S.C. 371 of International Application No. PCT/EP2009/064500 filed 3 Nov. 2009, which claims priority to German Application No. DE 10 2008 060 888.2 filed 9 Dec. 2008, the disclosures of which are expressly incorporated herein by reference.

The invention relates generally to a process for preparing acrolein, acrylic acid and water-absorbing polymer structures and also apparatuses for carrying out the process and their use, a process for purifying a glycerol phase and the use of a glycerol phase.

BACKGROUND

Acrylic acid is an important raw material in the plastics industry since it can be processed further to form polyacrylates and copolymers. Acrolein serves as starting material in the industrial synthesis of acrylic acid. An important industrial process for preparing acrolein is the partial oxidation of glycerol. This is obtained in large amounts in the cleavage or transesterification of glycerides.

In such glyceride cleavage processes or glyceride transesterification processes, an about 70-90% strength, often from 75 to 85% strength but usually about 80% strength, crude glycerol which, depending on the production process used, contains further components is obtained. The greatest secondary constituent is often from about 1% to about 20% of water. In addition, sodium and potassium salts of various mineral acids, for example salts of hydrochloric, sulfuric or phosphoric acid, are generally present. In some cases, salts of organic acids, for example of citric acid, are also present. In addition, free fatty acids and soaps are present in the crude glycerol. The undesirable organic constituents are referred to as MONG (for "matter organic non-glycerol").

When the crude glycerol produced in this way is used in subsequent synthesis processes on an industrial scale, the salts, in particular chlorides, cause corrosion problems. They therefore have to be removed from the crude glycerol. In the subsequent synthesis of acrolein, the organic constituents of the crude glycerol can lead to undesirable by-products and to problems in purification. In addition, they can, like the salts, have an undesirable effect on catalysts and lead to carbon deposits.

One process for preparing acrolein from glycerol and for further processing to give acrylic acid is known from WO-A-2006/092272. Here, the glycerol is obtained by cleavage of triglycerides and is processed further directly to give acrolein. The separation of acrolein from the reaction mixture is effected by means of distillation. In this process, even high-boiling constituents are removed. A remaining mixture, which contains high proportions of water and glycerol, is recirculated to the original reaction mixture for the synthesis of acrolein.

A further process is described in DE-A-10 2005 028 624. Here, acrolein is prepared from an aqueous glycerol phase. The acrolein is depleted from the resulting reaction product. The depleted reaction phase is recirculated in a circuit to the reaction region, so that unreacted glycerol can be converted into acrolein.

The processes of WO-A-2006/092272 and DE-A-10 2005 028 624 have the advantage that, because of the circuit via which the unreacted glycerol is returned to the synthesis, an overall higher proportion of the glycerol used is reacted.

However, a disadvantage is that in these processes part of the undesirable by-products, in particular the salts and the chloride ions, interfere in large-scale industrial use over the long term and lead to increased downtimes. WO-A-2006/092272 therefore proposes purifying the mixture comprising water and glycerol from the high boiler separator by means of a membrane. However, this only partly alleviates the disadvantage described. Many constituents, in particular the salts and the chloride ions, cannot be removed completely, if at all, by means of such a membrane. This can result in the problem that undesirable constituents increasingly accumulate in the circuit when the reaction is carried out for a prolonged time and these adversely affect the reaction or damage parts of the apparatus by corrosion.

SUMMARY

The present invention includes various embodiments as set forth herein.

It is an object of the present invention to at least partly overcome at least one of the disadvantages resulting from the prior art.

Furthermore, improved processes for preparing acrylic acid and polymerization products of acrylic acid, e.g. water-absorbing polymer structures, which are particularly suitable for industrial use should be provided. Processes which firstly can be carried out simply and efficiently and in which, secondly, very small amounts of undesirable by-products are obtained or accumulate when carrying out the process should be provided. The process of the invention should make it possible to utilize the reaction constituents very efficiently in one apparatus. In particular, a very small amount of salts and chloride ions should accumulate in a process according to the invention, so that corrosion damage and adverse effects on the oxidation reaction do not occur or are at least reduced, all in simple operation occurring without great interruptions.

A further object of the invention is to provide an integrated process for preparing acrolein and subsequent products, in which this preparative process can be carried out ideally without disruptions in a circuit.

A further object of the invention is to counter the accumulation of by-products such as salts and organic constituents at the stage of the glycerol solution fed in, so that the process also allows the use of crude glycerol which is obtained, for example, as by-product in biodiesel production.

A further object of the invention is to combine the process in an optimum way with upstream and downstream processes, so that the process can be carried out in a single integrated process and/or using a single apparatus. This applies particularly to processes for preparing acrylic acid and polymerization products of acrylic acid such as water-absorbing polymer structures.

A further object of the invention is to provide a process for preparing acrolein and subsequent products, in which glycerol-containing starting solutions and intermediates, in particular the crude glycerol obtained in the cleavage of fats or biodiesel production, can be purified in a very cheap and energy-saving way which is suitable for industrial use and can be used for preparing acrolein and subsequent products thereof. This applies particularly in connection with an ideally continuous way of carrying out the process.

Another object of the present invention was to provide a process for purifying a glycerol phase, preferably crude glycerol obtained in glyceride cleavage processes or glyceride transesterification processes, by means of which the glycerol phases can be purified particularly effectively.

Additional aspects of the present invention include feeding a further glycerol phase G3 into the process for preparing acrolein where the glycerol phase G3 has a higher glycerol content than the glycerol phase G2 produced in the process; where the glycerol phase G3 has a lower salt content than the glycerol phase G2; where the glycerol phase G3 has a lower content of organic compounds other than glycerol than the glycerol phase G2; where the glycerol phase G3 or the glycerol phase G2 or both glycerol phases comprise salts, fatty acids, soaps, monoglycerides, diglycerides, triglycerides and condensation products of glycerol as residual materials.

In additional aspects of the present invention, the separation in the process for preparing acrolein may be carried out by nanofiltration or reverse osmosis or both; or using wound modules comprising the polymeric nanofiltration membrane. In a further aspect, the wound module may have a feed spacer of at least 40 mm. In an additional aspect, the polymeric nanofiltration membrane may be made of a polyamide or a polyether sulfone. In an additional aspect, the separation may be carried out with a permeate yield of at least 90% by weight. In another aspect, the separation by means of the polymeric nanofiltration membrane may be carried out at a temperature of more than 40° C. In another aspect, the separation by means of the polymeric nanofiltration membrane may be carried out at a transmembrane pressure of more than 30 bar.

In further aspects of the present invention, at least one accompanying salt may at least be partly removed during the separation of the process for preparing acrolein, specifically in alternative steps i) and ii) described in further detail herein. In an element of this aspect, the separation in alternative steps i) and ii) may be carried out by electrodialysis followed by an osmotic purification. In a further aspect, the electrodialysis or, in another aspect of separation, the osmotic purification, may be followed by an ion-exchange treatment.

In a further aspect of the current invention, the process for preparing acrolein may include a acrolein reaction phase which may comprise a liquid other than water. In a further aspect, the acrolein reaction phase at the end of an acrolein reaction region may comprise a proportion of less than 50% by weight, or in the range from 0.1 to 50% by weight, based on the acrolein reaction phase, of glycerol. In a further aspect, the acrolein concentration in the acrolein reaction phase before the depletion according to process step (b) as described further herein may be at least 5% higher than after the depletion.

In another aspect of the current invention, the process for preparing acrolein may include a filtration unit which may comprise at least one microfilter (16), an ultrafilter (17), a nanofilter (18) or a combination of at least two thereof. In another aspect, the purification means of the process for preparing acrolein may comprise a nanofilter (18). In another aspect, the nanofilter (18) may comprise a polymeric nanofiltration membrane. In yet another aspect, the nanofilter may be made of a wound module comprising the polymeric nanofiltration membrane. In a further aspect, the wound module has a feed spacer of at least 40 mm. In another aspect, the polymeric nanofiltration membrane may be made of a polyamide or a polyether sulfone.

In an aspect of the current invention, the acrolein which can be obtained by the process for preparing acrolein or acrylic acid may be used as a basis of or in fibers, films, molding compositions, textile and leather auxiliaries, flocculants, coatings, paints and varnishes, foams, films, cables, sealing materials, liquid-absorbing hygiene articles, in particular diapers and sanitary napkins, supports for plant or fungal growth regulating agents or crop protection agents, additives for building materials, packaging materials or soil additives.

In one aspect of the current invention, in the process for purifying a glycerol phase G4, the glycerol phase G4 may have a glycerol content of more than 30% by weight, or more than 40% by weight, or more than 50% by weight, based on the total weight of the glycerol phase G4. In another aspect, at least one accompanying salt may be at least partly removed from the glycerol phase G4 in the process for purifying a glycerol phase G4. In one aspect of such a process, purification may be carried out by means of a polymeric nanofiltration membrane. In another aspect of such a process, the purification may be carried out using wound modules comprising the polymeric nanofiltration membrane. In another aspect, the wound module may have a feed spacer of at least 40 mm. In a further aspect, the polymeric nanofiltration membrane may be made of a polyamide or a polyether sulfone. In yet another aspect, the purification by means of the polymeric nanofiltration membrane may be carried out at a temperature of more than 40° C. In another aspect, the purification by means of the polymeric nanofiltration membrane may be carried out at a transmembrane pressure of more than 30 bar. In a further aspect, the permeate yield of purification that is carried out by means of a polymeric nanofiltration membranes may be at least 90% by weight.

FIGURES

The foregoing and other features, aspects, and advantages of the present invention will become better understood with regard to the following description, appended claims, and accompanying drawing where:

DETAILED DESCRIPTION

Figure 1:
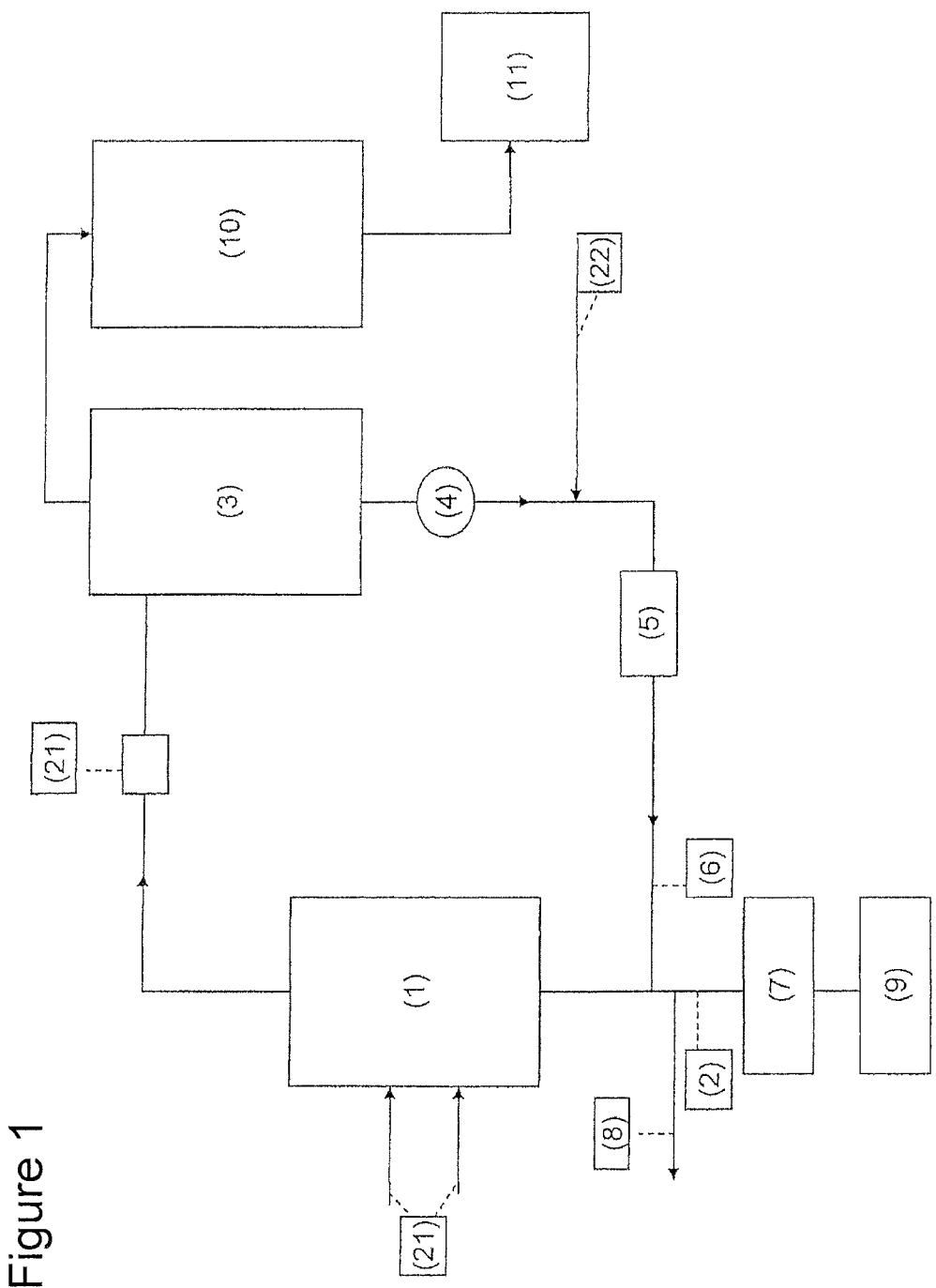
FIG. 1 is a schematic of an embodiment of an apparatus in accordance with the current invention.

A contribution to achieving at least one of these objects is provided by the subject matter of the category-forming claims, with secondary and dependent claims defining preferred embodiments of the present invention.

A contribution is provided, in particular, by a process according to the invention for preparing acrolein, which comprises the following steps:

(a) dehydration of an aqueous glycerol phase G1 in an acrolein reaction region to give an aqueous acrolein reaction phase;

(b) at least partial separation of the aqueous acrolein reaction phase into an acrolein-rich acrolein phase and a residue phase R1 which is low in acrolein compared to the acrolein phase, where the residue phase R1 comprises glycerol, water and residual materials other than glycerol and water;

(c) recirculation of at least part of the residue phase R1 to step (a);

wherein i) at least one of the residual materials present in a glycerol phase G2 comprising water, glycerol and residual materials other than glycerol and water is separated from the glycerol phase G2 and the purified glycerol phase G2 obtained in this way is fed directly to the acrolein reaction region or ii) at least one of the residual materials other than glycerol and water is separated off from a mixed phase M1 obtained by mixing a glycerol phase G2 comprising water, glycerol and residual materials other than glycerol and water with the low-acrolein residue phase R1 and the purified mixed phase M1 obtained in this way is fed to the acrolein reaction region.

Possible residual materials present in the low-acrolein residue phase R1 are in principle all by-products formed in the dehydration of glycerol to acrolein and also those by-products which are present in the aqueous glycerol phase G1 used in process step (a) and the subsequent products which may be formed therefrom in the dehydration. The proportion of the residual materials is generally in the range from 0.001 to 20% by weight, preferably in the range from 0.001 to 10% by weight and particularly preferably in the range from 0.001 to 5% by weight, in each case based on the low-acrolein residue phase R1. Solids such as tar products or carbonization products, oligomers of acrolein and oligomers of glycerol or the tar products or carbonization products of these oligomers are of particular importance.

A further contribution according to the invention is provided by a process for preparing acrylic acid, which comprises the steps:

(A1) provision of an acrolein-rich acrolein phase by the above-described process of the invention for preparing acrolein;

(A2) oxidation, preferably gas-phase oxidation over a gas-phase catalyst, of the acrolein-rich acrolein phase from step (A1) to give an acrylic acid phase; and (A3) optionally work-up of the acrylic acid phase to give acrylic acid.

In addition, a contribution according to the invention is provided by a process for preparing a polymer, which comprises the steps:

(P1) provision of an acrylic acid phase or an acrylic acid by the above-described process of the invention for preparing acrylic acid in a polymerization phase;

(P2) polymerization of the polymerization phase to give a polymer.

Processes for preparing acrolein are generally known from the prior art. In this respect, reference is made to WO-A-2006/092272 and DE-A-10 2005 028 624. The subject matter of both applications, in particular the disclosed processes for the synthesis of acrolein, acrylic acid and water-absorbing polymer structures and the apparatuses, is hereby expressly incorporated by reference. The purification according to the invention as per alternatives i) and ii) can be used in these processes.

In step (a) of the process of the invention for preparing acrolein, an aqueous glycerol phase G1 is dehydrated in an acrolein reaction region to give an aqueous acrolein reaction phase. Here, the term "acrolein reaction region" refers to the part of the apparatus in which the dehydration of glycerol to form acrolein is carried out.

The dehydration of the glycerol can, in a preferred embodiment of the invention, take place in a liquid phase. In a further preferred embodiment of the invention, the dehydration is carried out in the gas phase. The dehydration can also be carried out in a combined process in which liquid- and gas-phase dehydration are combined.

In this context, the corresponding processes disclosed in WO-A-2006/092272 are expressly incorporated by reference.

Preference is given, according to the invention, to the pressure in the acrolein reaction region being at least 50 bar, preferably at least 80 bar and particularly preferably at least 120 bar and more preferably at least 140 bar. The acrolein reaction region is thus configured as a pressure region which is bounded at its beginning by a pressure generator, e.g. a pump, and at its end by a pressure regulator, e.g. a pressure valve and more preferably a pressure regulating valve. The dehydration reaction in process step (a) occurs in at least part of the acrolein reaction region. The acrolein reaction region is usually at least partly tubular and designed for a maximum pressure of 500 bar and a maximum temperature of 600° C., which are sufficient for carrying out the process of the invention.

In addition, preference is given, according to the invention, to the temperature in the acrolein reaction region being at least 80° C., preferably at least 180° C., particularly preferably at least 230° C. and more preferably at least 280° C. and even more preferably at least 320° C. The temperatures can be achieved, firstly, via the pressure conditions in the acrolein reaction region and also via appropriate heating of the acrolein reaction region.

In general, the pressure and/or temperature conditions in the acrolein reaction region are selected so that the acrolein reaction phase and in particular the water present therein are at least close to or at least partly in the supercritical range.

In addition, preference is given, in the process according to the invention, to the acrolein reaction region comprising, in addition to the reaction mixture, a dehydration catalyst. This is preferably present in an amount in the range from 0.001:1000 to 10:1000, more preferably from 0.01:1000 to 5:1000 and particularly preferably from 0.04:1000 to 1:1000, in each case based on the amount of glycerol used in the acrolein reaction phase.

In a preferred embodiment of the process of the invention, the dehydration catalyst can be present either as acid or as base or as a combination thereof. If the dehydration catalyst is present as acid, it is a compound apart from water which likewise acts as strong acid having acidic properties close to the or in the supercritical range. If the dehydration catalyst is an acid, both inorganic and organic acids are possible. Possible inorganic acids are, in particular, acids of phosphorus such as $H_3PO_4$, of sulfur such as $H_2SO_4$, of boron such as $B(OH)_3$ or a mixture thereof. In a further embodiment of the dehydration catalyst, it is present as superacid, which by definition has a low pKa of <−1. When the dehydration catalyst is present as organic acid, preference is given to alkylsulfonic acids, with trifluoromethanesulfonic acid or methanesulfonic acid or mixtures thereof being particularly preferred. Possible bases for the dehydration catalyst are, in particular, aluminum, lanthanum, alkali metal or alkaline earth metal oxides, hydroxides, phosphates, pyrophosphates, hydrogenphosphates or carbonates or mixtures of at least two thereof, which can in each case also be supported.

Furthermore, the dehydration catalyst can be present either as a solid or a liquid at room temperature. Dehydration catalysts present as solid also include liquid dehydration catalysts immobilized on a solid support. Preferred solid dehydration catalysts are, in particular, compounds comprising silicon oxide, e.g. zeolites. In addition, Ti, Zr or Ce oxides, sulfated oxides and phosphated oxides or mixtures of at least two thereof are also possible. A series of dehydration catalysts is described in detail in DE-A-42 38 493, so that the disclosure of this document is incorporated by reference in this context.

Furthermore, the acrolein reaction phase preferably comprises a liquid other than water in the process of the invention. When liquid dehydration catalysts are used, this liquid should also be different from the catalysts. These liquids have the function of solubility improvers. In general, possible liquids of this type are organic compounds which are miscible with water at 20° C. and have at least one heteroatom, preferably two heteroatoms, and are inert toward the other constituents of the acrolein reaction phase. Such liquids are, for example, hydroxypiperidine or aprotic and polar liquids such as sulfolane, diglyme, tetraglyme, dioxane, trioxane or γ-butyrolactone. Furthermore, compounds or solutions of compounds which display a chelating action are possible as liquids. In this context, possibilities are, for example, EDTA, NTA or DPTA, as can be obtained under the trade names Versene®, Versenex®, Entarex® or Detarex®, or else crown ethers.

Furthermore, preference is given, in the process of the invention, to the acrolein reaction region comprising a metal or a metal compound or both. Preference is given here to monovalent, divalent or polyvalent metals or metal compounds. In addition, this metal or these metal compounds are preferably different from the metal or metals used for construction of the acrolein reaction region. Likewise, in one embodiment of the invention, these metals or metal compounds are immobilized, either directly or indirectly by means of a bonding agent, on the material used for construction of the acrolein reaction region. However, these metals or metal compounds can also be present in particulate form in the acrolein reaction region. In general, it is preferred that these metals or metal compounds cannot be discharged from the acrolein reaction region by a liquid or gas stream. Apart from immobilization of these metals or metal compounds, this can be achieved in the case of these metals or metal compounds being present in particulate form by means of sieves or filters present in the acrolein reaction region. Furthermore, in one embodiment of the process of the invention, the metals or metal compounds are selected so that the above-mentioned liquids can coordinate or even complex to these metals or metal compounds. In addition, preference is given, in the process of the invention, to these metals being present as metal compounds, with metal salts or metals complexed by ligands being particularly preferred. Possible ligands are, in particular, carbon monoxide, e.g. carbonyl, triphenylphosphine, Cp, Cp* or AcAc. The metal salts are, in particular, used in the form of their sulfates or phosphates. As metals, mention may be made of tin, in particular as tin sulfate, zinc, in particular as zinc sulfate, lithium, in particular as lithium sulfate, magnesium, in particular as magnesium sulfate, copper, in particular as copper sulfate, palladium, in particular as palladium-carbonyl complex, which is usually used as acetate, rhodium, in particular as rhodium-carbonyl complex, which is usually used as acetate, ruthenium, in particular as ruthenium-carbonyl complex, which is usually used as acetate, nickel, in particular as nickel-carbonyl complex, which is usually used as acetate, iron, in particular as iron-carbonyl complex, cobalt, in particular as cobalt-carbonyl complex, cesium, in particular as cesium acetate, and lanthanides, in particular lanthanum, or a mixture of at least two thereof. The metals are preferably used as salts with complexing agents, often also in the presence of carbon monoxide. Further metal compounds which may be mentioned are heteropolyacids. Among these heteropolyacids, preference is given to those which are formed when different acid molecules of a metal such as chromium, tungsten or molybdenum and a nonmetal, preferably phosphorus, are combined with elimination of water. Heteropolyacids are, for example, phosphotungstic acids, silicotungstic acids or silicomolybdic acids and also the corresponding vanadium compounds.

Furthermore, the residence time of the acrolein reaction phase in the acrolein reaction region is preferably in the range from 1 to 10 000 seconds, more preferably in the range from 5 to 1000 seconds and particularly preferably in the range from 10 to 500 seconds, in the process of the invention.

In addition, it has been found to be helpful in the process of the invention for the acrolein reaction phase to comprise carbon monoxide in the range from 0.0001 to 10% by weight, preferably from 0.001 to 7% by weight and more preferably from 0.005 to 5% by weight, in each case based on the acrolein reaction phase. This measure can be advantageous for reducing the amount of secondary components.

In addition, preference is given, in the process of the invention, to the acrolein reaction phase at the end of the acrolein reaction region comprising a proportion of <50% by weight, preferably <25% by weight and more preferably <15% by weight, in each case based on the acrolein reaction phase, of glycerol. These process conditions give, after carrying out process step (b), an acrolein phase which can be fed into stage (A2) of the process of the invention for preparing acrylic acid for a significantly longer period of time without an appreciable deterioration of the conversion of acrolein into acrylic acid occurring. Furthermore, it is generally the case in the process of the invention that the glycerol concentration at the beginning of the acrolein region is greater than at the end of the acrolein reaction region and preferably decreases continuously to the end. Preference is also given, according to the invention, to the acrolein reaction phase at the end of the acrolein reaction region comprising a proportion in the range from 0.1 to 50% by weight, preferably from 5 to 45% by weight and even more preferably from 10 to 40% by weight, in each case based on the acrolein reaction phase, of acrolein.

Furthermore, it is preferred that at least part of the acrolein reaction phase is present in gaseous form in the process of the invention. Preference is also given to the acrolein reaction phase in the acrolein reaction region to be present in at least two states of matter. These states of matter are preferably liquid and gaseous. When at least part of the acrolein reaction phase is present as gas, the concentration of acrolein in this acrolein reaction gas phase is preferably higher than in the part of the acrolein reaction phase which has a state of matter different from the acrolein reaction gas phase. The high acrolein concentration in the acrolein reaction gas phase makes partial removal or removal of the acrolein significantly easier because the acrolein reaction gas phase having a high concentration of acrolein can be discharged from the acrolein reaction region by means of appropriate pressure regulation and acrolein can subsequently be obtained in high concentration by depressurization.

The purer the acrolein obtained in this way, the less need there is for cooling via a heat exchanger or further separation, which is generally carried out by distillation, in a separation unit in addition to the depressurization, which can, for example, be effected via a pressure regulator configured as a pressure regulating valve. It is also possible for the acrolein phase leaving the acrolein reaction region to be passed through a plurality of units comprising a relief valve and a heat exchanger and connected in series before the acrolein phase which has been treated in this way is fed to a separation unit. The pressure difference from before the pressure regulator in the acrolein reaction region to after the pressure regulator is preferably at least 30 bar, more preferably at least 60 bar and still more preferably at least 100 bar. Furthermore, preference is given, in the process of the invention, to the acrolein in the acrolein reaction region to be at least partly present in the supercritical state, which contributes to an increase in yield.

Furthermore, it is advantageous in the process of the invention for the acrolein reaction phase before partial separation as per process step (b) to be under a higher pressure than during partial separation. Preference is also given, according to the invention, to the acrolein concentration in the acrolein reaction phase before the partial separation as per process step (b) being at least 5% higher, preferably at least 10% higher and particularly preferably at least 50% higher, than after the partial separation. Furthermore, preference is given to using an entrainer gas in the process of the invention. This entrainer gas is preferably fed in before the acrolein reaction region and serves to discharge the acrolein reaction phase. In this context, too, it is advantageous to have as much acrolein as possible in a gaseous part of the acrolein reaction phase. Possible entrainer gases are in principle all gases known to those skilled in the art which are inert toward the compounds participating in the above processes. Examples of such entrainer gases are nitrogen, air, $CO_2$, water or argon. Preference is thus given in the process of the invention to at least part of the entrainer gas being fed back into the acrolein reaction region after having passed through the acrolein reaction region. This introduction can be carried out directly before the acrolein reaction region or at any other point upstream of the acrolein reaction region and can, for example, be utilized to build up an admission pressure of the starting materials, which can be increased further by means of an appropriate pump to the pressure conditions necessary for the acrolein reaction region.

In process step b) of the process of the invention for preparing acrolein, an at least partial separation of the aqueous acrolein reaction phase into an acrolein-rich acrolein phase and a residue phase R1 which is low in acrolein compared to the acrolein phase, where the residue phase R1 comprises glycerol, water and residual materials other than glycerol and water, takes place, with this separation preferably being carried out by means of a distillation in which the residue phase R1 is preferably obtained as bottom product.

In process step (c) of the process of the invention for preparing acrolein, at least part of the residue phase R1 is recirculated to step (a).

The process of the invention for preparing acrolein then provides that
i) at least one of the residual materials present in a glycerol phase G2 comprising glycerol, water and residual materials other than glycerol and water is separated from the glycerol phase G2 and the purified glycerol phase G2 obtained in this way is fed directly to the acrolein reaction region or
ii) at least one of the residual materials other than glycerol and water is separated off from a mixed phase M1 obtained by mixing a glycerol phase G2 comprising glycerol, water and residual materials other than glycerol and water with the low-acrolein residue phase R1 and the purified mixed phase M1 obtained in this way is fed directly to the acrolein reaction region.

The formulation "where the purified glycerol phase G2 is fed directly to the acrolein reaction region", as used in relation to alternative i) of the process of the invention for preparing acrolein, is intended to express that the purified glycerol phase is fed without further purification to the acrolein reaction region. However, this does not rule out the addition of further streams, for example a further glycerol phase, in particular, for example, technical-grade glycerol, to the purified glycerol phase G2 before the latter enters the acrolein reaction region. An analogous situation also applies to the formulation "where the purified mixed phase M1 obtained in this way is fed directly to the acrolein reaction region" in relation to alternative ii) of the process of the invention for preparing acrolein.

According to the invention, the glycerol phase G2 is preferably a crude glycerol phase which is obtained as a reaction product in the cleavage or transesterification of triglycerides, for instance in the course of biodiesel production.

The glycerol phase G2, preferably the above-described crude glycerol, usually comprises, in addition to glycerol and water, further residual materials, in particular from the group consisting of salts, fatty acids, soaps, monoglycerides, diglycerides, triglycerides and condensation products of glycerol. The water content of the crude glycerol is usually in the range of from about 5 to about 25% by weight, in particular in the range from about 15 to 20% by weight, in each case based on the glycerol phase G2, preferably the crude glycerol. The proportion of glycerol is usually in the range from 70 to 90% by weight, in particular from 75 to 85% by weight, in each case based on the glycerol phase G2, preferably the crude glycerol. The salts are, in particular, alkali metal salts of inorganic and organic acids. They are in particular sodium and potassium salts. The salts are usually those of hydrochloric, sulfuric, phosphoric or citric acid. It should be noted that the respective composition of a glycerol phase G2, preferably a crude glycerol phase, is dependent firstly on whether it originates from cleavage of fats or transesterification of fats, (i.e., for example, biodiesel production) and secondly on the purity of the animal or vegetable oils or fats used for the cleavage or transesterification of the fats.

In the context of such a crude glycerol phase as glycerol phase G2, the separation of residual materials from the glycerol phase G2 or from the mixed phase M1 means that the proportion of at least one residual material from these compositions is reduced by at least 10%, preferably at least 20%, more preferably at least 50% and particularly preferably at least 80 or 90%. This applies in particular to the proportion of the salts or individual ions, in particular chloride ions. In a preferred embodiment of the invention, the proportion of chloride ions in the glycerol phase G2 or in the mixed phase M1 is reduced to such an extent that the proportion of chloride ions in the acrolein reaction phase is <50 ppm, preferably <20 ppm, particularly preferably <5 or <10 ppm. The glycerol phase G2 and/or the mixed phase M1 after removal of the residual materials preferably has such a purity that reduced corrosion or essentially no corrosion of the apparatus takes place and/or the synthesis of the acrolein is not adversely affected or adversely affected to a lesser extent.

In a particular embodiment of the invention, the preparation of crude glycerol by cleavage of glycerides and the subsequent further processing of the glycerol to form acrolein are carried out in a single continuous process. However, it is also possible to produce the crude glycerol separately and introduce it into the process of the invention.

The removal of residual materials as per alternative i) or ii) is preferably carried out by means of at least one, preferably at least two and more preferably each of the following methods of separation:
($\alpha$1) distillation;
($\alpha$2) filtration, preferably selected from the group consisting of a microfiltration, an ultrafiltration, a reverse osmosis, a nanofiltration or at least two thereof;
($\alpha$3) electrodialysis;
($\alpha$4) ion-exchange treatment;
($\alpha$5) treatment with activated carbon.

In principle, the above methods of separation can be combined in any order which is known to those skilled in the art and appears to be suitable. Furthermore, it is also possible to combine the same method of separation two or more times, preferably with the same methods of separation being separated by at least one method of separation which is different from these. Thus, each method of separation can represent an embodiment of the process of the invention. The combinations and sequences of methods of separation represented by the following sequences of symbols likewise each represent an embodiment of the process of the invention: α1α2, α1α3, α1α4, α2α3, α2α4, α3α4, α2α5. According to the invention, particular preference is given to the separation being carried out by nanofiltration, reverse osmosis or both. Furthermore, a separation by means of nanofiltration followed by a treatment with activated carbon can be advantageous.

The abovementioned methods of separation should, in particular, make it possible to remove at least part, preferably at least 10% by weight and particularly preferably at least 60% by weight, of the accompanying salts from the crude glycerol when crude glycerol is used as glycerol phase G2.

If the separation is carried out by means of distillation (α1), this can be carried out in two or more stages. Preference is given to the second or each further stage being carried out at a pressure lower than that in the first stage. The second or further stage is preferably carried out at a pressure in the range from 20 to 400 mbar, preferably in the range from 30 to 300 mbar and particularly preferably in the range from 50 to 150 mbar. The first stage is usually carried out at a pressure in the range from 500 mbar to 1 bar.

Furthermore, the separation can be carried out by means of filtration (α2). In this context, preference is given, in a particularly preferred embodiment of the process of the invention for preparing acrolein in which the crude glycerol from cleavage of fats or transesterification of fats is used as glycerol phase G2, to the separation as per process variants i) and ii) being carried out by nanofiltration, reverse osmosis or a combination of these methods, but particularly preferably by nanofiltration. It has surprisingly been found that the aqueous glycerol solutions, for example crude glycerol, can, in contrast to pure glycerol, be purified at a very high permeate flux by means of nanofiltration, with a considerable part of the salt burden present in the crude glycerol being able to be separated off.

Nanofiltration (NF) is a membrane separation process which is between the separation limits of reverse osmosis and of ultrafiltration. The operating pressure is preferably in the range from 0.3 to 4.0 MPa. The exclusion limits are preferably in the range from 100 to 3000 dalton, particularly preferably from 180 to 2000 dalton. The selectivity of an NF membrane is determined mainly by two different parameters. Firstly, the retention is dependent on the size of the compounds, i.e. on the molecular weight. However, the retention and the permeability of NF membranes are also significantly dependent on the electric charge and valence of the salts and compounds in solution. Dilute solutions of monovalent ions can pass largely unhindered through an NF membrane, while polyvalent ions (for example sulfate and carbonate) are retained to a large degree.

The nanofiltration is preferably carried out by means of a polymeric nanofiltration membrane which is preferably present in a wound module.

Wound modules to be used according to the crossflow principle are known, for example, from DE 43 28 407 C1. They comprise a housing having a wound structure enclosed therein. In such a wound module, the membranes have the shape of bags welded shut on three sides with a porous membrane support in the interior of the bag. They are wound together with a separation braid (feed spacer) around a perforated central tube. The solution to be filtered, for example the crude glycerol to be filtered (feed), flows under high pressure in the axial direction through the gap between the membrane bags, with part of the water and the glycerol permeating through the membrane into the bags and flowing spirally around the central collection tube in the membrane support. The permeate goes through the unwelded side of the bag adjoined to the central tube into the latter and is there conveyed out of the module.

In connection with such a wound module, it is also advantageous for it to have a feed spacer having a thickness of at least 40 mm, particularly preferably at least 45 mm and most preferably at least 50 mm.

Possible nanofiltration membranes for the purposes of the invention are, in particular, polymeric nanofiltration membranes which are made of a polyamide or a polyether sulfone. However, apart from these types of membrane, it is in principle also possible to use all nanofiltration membranes which are known to a person skilled in the art from the prior art. Mention may also be made here of, in particular, membranes based on polysulfone, polyacrylonitrile, polyethylene, Teflon, porous carbon, ceramic, cellulose acetate, polyurea, aromatic or aliphatic polyamides, sulfonated polyaryl ethers, polyfuran, polybenzimidazole, various fluoro polymers, polyether aromatics such as polyimide or polyimidazopyrrolidone or similar materials. Further nanofiltration membranes which are suitable for the purposes of the invention are, in particular, the membranes which can be obtained under the trade name "Nadir N30F" from Microdyn-Nadir GmbH and under the names "DESAL 5DK" and "DESAL 5□L" from GE Osmonics, USA.

The use of nanofiltration membranes having an exclusion size of 2000 kDa or less, particularly preferably 1500 kDa or less, even more preferably 1000 kDa or less and most preferably 500 kDa or less, is particularly advantageous according to the invention.

In connection with the separation by means of nanofiltration, preference is also given to the separation being carried out at a permeate yield of at least 90% by weight, particularly preferably at least 95% by weight and most preferably at least 99% by weight.

Furthermore, preference is given, in the separation by means of nanofiltration, to this separation being carried out at a temperature of preferably more than 40° C., particularly preferably more than 45° C. and most preferably more than 50° C., and at a transmembrane pressure of preferably more than 30 bar, particularly preferably more than 40 bar and most preferably more than 50 bar.

In reverse osmosis, pressure is utilized to reverse the natural osmosis process. The medium in which the concentration of a particular material is to be reduced is separated by a semipermeable membrane from the medium in which the concentration is to be increased. The first medium is placed under a pressure which has to be higher than the pressure generated by osmosis to concentration equilibration. As a result, the molecules of the solvent can migrate in the direction opposite to their "natural" osmotic direction of travel into the region in which the dissolved materials already have a lower concentration. Ultrafiltration is primarily a pressure-driven separation process which is dependent on the particle size and is based on a sieve effect. Ultrafiltration membranes preferably have a pore size in the range from 0.5 to 200 nm, in particular from 1 to 100 nm, and are preferably able to retain compounds having a molecular weight of more than 200 dalton, in particular more than 300 dalton.

Apart from the nanofiltration which is most preferred according to the invention and apart from ultrafiltration, microfiltration can also be used as separation process as per variants i) and ii) of the process of the invention for preparing acrolein if the separation is carried out by means of filtration (α2). In a microfiltration (MF), a membrane is used for separating particles from aqueous solutions in a preferably pressure-driven process. Microfiltration is a filtration of colloidal or other finely divided particles having a linear dimension of from about 0.02 μm to about 10 μm. The typical operating pressure of an MF is comparatively low and is in the range from 0.02 MPa to 0.5 MPa.

Furthermore, the separation can be carried out by means of electrodialysis (α3). Electrodialysis is a separation process in which ions are transported through a semipermeable membrane under the influence of an electric potential. The membranes used are permeable only to positively or negatively charged ions, i.e. they operate cation- or anion-selectively. Cation-selective membranes are polyelectrolytes comprising negatively charged matter which retain negatively charged ions and are permeable to positively charged ions. Arrangement of a plurality of chambers which are alternately bounded by anion- and cation-selective membranes enable ions to be removed from the solution. The chambers are located between the sheet-like electrodes anode and cathode. The arrangement enables the ions of the solution to be concentrated in some chambers while they can leave the solution in other chambers. The solutions having an increased salt concentration are combined to give the "concentrate" while the low-salt solutions form the "diluate". The concentrated solution is circulated until a final concentration is reached and is subsequently discharged. This process is particularly suitable for the removal of ions from aqueous solutions. Uncharged particles, on the other hand, cannot be eliminated. Cation-selective membranes preferably comprise sulfonated polystyrene, while anion-selective membranes are preferably made up of polystyrene having quaternary amine groups. A pretreatment of the solution is sometimes necessary before the electrodialysis process. In a particular embodiment, suspended solids, in particular those having a diameter of more than 10 mm, are removed beforehand in order to avoid blocking of the membrane pores. A reversal of the flow direction can be provided in electrodialysis. Regular removal of deposits can be achieved in this way.

Furthermore, separation by means of an ion-exchange treatment (α4) is also conceivable. An ion-exchange treatment is carried out in apparatuses by means of which ions dissolved in water are replaced by other ions. These are, for example, columns filled with an ion-exchange material, viz. the ion-exchange resin, and through which the solution to be treated flows. The ions to be replaced are bound to the ion-exchange material which in turn releases ions into the solution. According to the invention, salt ions of the solution are preferably replaced by protons and hydroxy ions, so that salts are overall removed from the solution. In specific embodiments of the invention, the ion-exchange treatment according to the invention is not an electrodialysis, no electric potential is applied and/or no elevated pressure is used.

In a particular embodiment of the process of the invention, the residual materials other than water and glycerol are separated off in process variants i) and ii) by means of filtration, particularly preferably a nanofiltration or a reverse osmosis, most preferably by a nanofiltration, followed by an electrodialysis. In this context, it can also be advantageous for the electrodialysis to be followed by an osmotic purification, preferably a further purification by reverse osmosis, with the electrodialysis or reverse osmosis in turn being able to be followed by an ion-exchange treatment.

In another particular embodiment of the process of the invention, the residual materials other than water and glycerol are separated off in process variants i) and ii) firstly by means of a filtration, particularly preferably a microfiltration, a nanofiltration or a reverse osmosis, most preferably by a microfiltration, followed by an electrodialysis, followed by a further filtration, particularly preferably a nanofiltration or a reverse osmosis, and in turn followed by an ion-exchange treatment.

In a further preferred embodiment of the invention, an integrated membrane system for salt removal, in which electric separation methods are combined with separation steps over membranes under superatmospheric pressure are used for separating residual materials from the glycerol phase G2, preferably from the crude glycerol, or from the mixed phase M1. Here, an electrodialysis is combined with a nanofiltration or reverse osmosis. Appropriate apparatuses are described in WO-A-2006/074259, which is hereby expressly incorporated by reference. The invention provides, in a preferred embodiment, a process according to the invention for preparing acrolein, in which the purification of a glycerol-containing solution is carried out using an apparatus as described in WO-A-2006/074249. It is surprising that such an apparatus can also be used for purifying highly concentrated glycerol solutions.

In a particular embodiment of the process of the invention for preparing acrolein, a further glycerol phase G3 is fed in addition to the purified glycerol phase G2 or the purified mixed phase P1 into the acrolein reaction region. In this context, it is particularly preferred that the glycerol phases G3 and G2 differ in terms of their glycerol content or salt content or in their content of organic compounds other than glycerol or in at least two of these contents. Particular preference is given to the glycerol phase G3 having a higher glycerol content than the glycerol phase G2 and/or a lower salt content than the glycerol phase G2 and/or a lower content of organic compounds other than glycerol than the glycerol phase G2. The contents of the glycerol phases G2 and G3 in respect of glycerol, the salt and the organic compounds other than glycerol often differ by at least 1% by weight, preferably at least 2% by weight and more preferably at least 5% by weight, in each case based on the respective glycerol phase.

If, as described above, a further glycerol phase G3 is fed in addition to the purified glycerol phase G2 or the purified mixed phase P1 into the acrolein reaction region, it is also preferred, when crude glycerol is used as glycerol phase G2, that the glycerol phase G3 is a distillate obtained in the distillation of crude glycerol obtained in the cleavage or transesterification of triglycerides. This distillate is conventionally referred to as "technical-grade glycerol". Technical-grade glycerol usually has a glycerol content of at least 70% by weight, in particular at least 80% by weight and preferably at least 90% by weight. The water content is usually up to 30% by weight, preferably up to 20% by weight and more preferably up to 10% by weight. As residual materials other than glycerol and water, the glycerol phase G3 preferably comprises salts, fatty acids, soaps, monoglycerides, diglycerides, triglycerides and condensation products of glycerol. The other residual materials to be encountered in crude glycerol are at least ten times lower in concentration than in technical-grade glycerol. The bottom product obtained in the preparation of technical-grade glycerol by means of distillation can pass through a salt separator and subsequently optionally be fed at least partly, preferably in a proportion of at least 10% by weight, particularly preferably at least 50% by weight and more preferably in an amount in the range from 20 to 99.9999% by weight, back to the distillation of the crude glycerol in order to achieve a further increase in the yield of glycerol in the purification of the crude glycerol.

Furthermore, it has been found to be useful in the distillation of the crude glycerol for at least part of the distillate obtained, preferably at least 50% by weight, particularly preferably at least 75% by weight or a proportion in the range from 60 to 100% by weight, of the distillate to pass through an ion exchanger. Furthermore, it can be found to be advantageous to allow the distillation to occur at different pressures in a first stage and at least one further stage, with the pressure difference being at least 0.1 bar, preferably at least 1 bar and particularly preferably at least 2 bar. Furthermore, preference is given, in the process of the invention, to allowing the distillation in a first stage to occur at a higher pressure than the distillation in the at least one further stage.

In another inventive embodiment of the process in which purified glycerol obtained from crude glycerol is used as further glycerol phase G3, the purification of the crude glycerol is preferably carried out by filtration and an electrodialysis and subsequently a nanofiltration, reverse osmosis or ion-exchange treatment or at least two of these further purifications as further purification. In the case of the combination of electrodialysis and nanofiltration, the terms HEEPM™, utilizing, inter alia, the HEED® process, refer to a variant of the process offered by EET Corporation, USA. These are particularly advisable for the removal of salts.

In a further inventive embodiment of the process, the glycerol phase G3 preferably comes from a purification in which crude glycerol is firstly subjected to a filtration for separating off solids, preferably a microfiltration, and subsequently to an electrode dialysis. Here, preference is given to the electrodialysis being followed by a filtration, preferably a nanofiltration or reverse osmosis or a combination of both separation methods. In addition, preference is here given to the filtration, preferably the nanofiltration or the reverse osmosis or the combination of these two separation methods, being followed by an ion-exchange treatment.

As residual materials, the glycerol phase G3 or the glycerol phase G2 or both usually comprise salts, fatty acids, soaps, monoglycerides, diglycerides, triglycerides and condensation products of glycerol.

1. In a first preferred embodiment of the process of the invention for preparing acrolein, preference is given to the glycerol phase G2 being crude glycerol which has been obtained, for example, from the cleavage of fats or transesterification of fats and is added to the residue phase R1, with residual materials subsequently being separated off from the resulting mixed phase M1 by means of a filtration, particularly preferably by means of the above-described nanofiltration. Before this separation by nanofiltration, the mixed phase M1 can optionally also be purified by means of a prefiltration in order to separate off solids present in this mixed phase. Furthermore, in this first particular embodiment, technical-grade glycerol can also be used as further glycerol phase G3 in addition to the use of crude glycerol in the above-described way, with in this case preference being given to the technical-grade glycerol either being fed directly to the acrolein reaction region or else firstly being added to the purified mixed phase M1 and the composition obtained in this way then being fed to the acrolein reaction region. This first particular embodiment of the process of the invention for preparing acrolein thus realizes variant ii) of the process of the invention for preparing acrolein. This embodiment of the process of the invention is particularly suitable for use of crude glycerol having low chloride contents, preferably having chloride contents of less than 1 g/l.

2. In a second particular embodiment of the process of the invention for preparing acrolein, preference is given to the glycerol phase G2 being crude glycerol which has been obtained, for example, from the cleavage of fats or transesterification of fats and is added to the residue phase R1, with residual materials subsequently being separated off from the resulting mixed phase M1 by filtration, particularly preferably by means of the above-described nanofiltration. This filtration is also followed by purification by means of electrodialysis, which may optionally be followed by an ion-exchange treatment. In this second particular embodiment of the process of the invention, too, it can be found to be advantageous to purify the mixed phase M1 to separated off solids present in this mixed phase optionally also by means of a prefiltration and/or an ion exchanger before removal of residual materials by nanofiltration. If appropriate, in this second particular embodiment, too, technical-grade glycerol can also be used as further glycerol phase G3 in addition to the use of crude glycerol in the above-described way, with preference being given in this case to the technical-grade glycerol being introduced either directly into the acrolein reaction region or else firstly being added to the purified mixed phase M1 and the composition obtained in this way then being introduced into the acrolein reaction region. This second particular embodiment of the process of the invention for preparing acrolein thus likewise realizes variant ii) of the process of the invention for preparing acrolein. This embodiment of the process of the invention is particularly suitable for use of crude glycerol having relatively high chloride contents, preferably having chloride contents of more than 1 g/l.

3. In a third particular embodiment of the process of the invention for preparing acrolein, preference is given to the glycerol phase G2 being crude glycerol which has been obtained, for example, from the cleavage of fats or transesterification of fats, with residual materials firstly being separated off from this crude glycerol by means of distillation, followed by a further removal of residual materials by means of an ion exchanger and the resulting purified glycerol phase G2 then being fed, optionally after combination with a further glycerol phase, in particular after combination with technical-grade glycerol, and optionally after combination with purified residue phase R1, to the acrolein reaction region. The residue obtained in the distillation of the crude glycerol can be treated by means of a salt separator. Apart from the removal of residual materials from the glycerol phase G2 by a combination of distillation and ion exchange, the purification can also be carried out by filtration, in particular by means of the above-described nanofiltration. Residual materials are subsequently likewise separated off from the residue phase R1 obtained after separation of the aqueous acrolein reaction phase in process step b) to give a purified residue phase R1, with this separation preferably being carried out by filtration, particularly preferably by means of the above-described nanofiltration. Here too, it can be found to be advantageous to purify the mixed phase M1 by prefiltration to separate off solids present in this mixed phase before the above-described separation by nanofiltration. The purified residue phase R1 can then be fed directly to the acrolein reaction region or firstly be added to the purified crude glycerol phase, as described above. This third particular embodiment of the process of the invention for preparing acrolein thus realizes variant i) of the process of the invention for preparing acrolein.

In this third particular embodiment of the process of the invention for preparing acrolein, at least part of the glycerol solution which has been purified according to the invention can be taken from the process before being transferred back into the acrolein reaction region. The purified glycerol preferably has the quality of technical-grade glycerol. The purified glycerol solution obtained in this way can be used for further applications, for example for other synthetic processes.

The processes described generally have the advantage that after the removal of the acrolein in the distillation unit and the removal of the depleted reaction phase (process step b), the further purification is carried out without a further distillation being required. The purification measures are comparatively inexpensive and low in energy and subject the respective glycerol-containing solutions to only mild conditions because of the comparatively low temperatures which are employed. The removal of salts from the glycerol-containing solution is achieved stepwise by means of the combination of these purification steps.

A further advantage is that the purified glycerol obtained has a good color number since it has not been thermally stressed. In addition, a high purity is achieved by means of the specific inventive combination of the purification steps. The process is particularly suitable for purifying crude glycerol having high proportions of salts, chlorides and organic substances.

Furthermore, an embodiment of the process of the invention provides for part, preferably at least 5% by weight, more preferably at least 35% by weight and even more preferably at least 50% by weight, or from 15 to 35% by weight, of the glycerol of the glycerol phase G1 being circulated as feed stream to the dehydration in the process for preparing acrolein. In this way, it is possible by selection of the correct flow rates, firstly to slow or completely prevent the formation of deposits and, secondly, to control the reaction precisely.

In the recirculation in the recycle mode of operation, the recirculated stream is generally set so that high acrolein yields are obtained at very high conversions. The recycle ratio of the glycerol phase to the recirculated low-acrolein residue phase R1 is preferably in the range from 0.01:10 to 9:10, preferably from 0.1:10 to 5:10 and particularly preferably from 0.5:10 to 3:10. The recirculation serves, in particular, to optimize utilization of the starting materials, to save costs and to protect the environment.

In the process of the invention for preparing acrylic acid, preference is given to the acrolein phase in step (A2) comprising from 0.1 to 50% by weight, preferably from 5 to 30% by weight, more preferably from 7 to 20% by weight and even more preferably from 10 to 20% by weight, in each case based on the acrolein phase, of acrolein. In connection with an ideally long running time of the oxidation reactor, the acrolein phase preferably comprises less than 10% by weight, more preferably less than 5% by weight and particularly preferably less than 2% by weight, of constituents which are generally referred to has high boilers and have a boiling point higher than that of acrolein. Preference is also given to the acrolein phase containing less than 10% by weight, more preferably less than 5% by weight and particularly preferably less than 2% by weight, in each case based on the acrolein phase, of low boilers, i.e. substances which have a boiling point lower than that of acrolein. Furthermore, preference is given to the acrolein phase comprising, in addition to acrolein and any low and high boilers present, essentially inert constituents, in particular gaseous constituents, which adversely affect the oxidation reaction in step (A2) only insignificantly, if at all.

In addition, preference is given, in the process of the invention for preparing acrylic acid, to a gaseous acrylic acid phase comprising acrylic acid being formed in the oxidation in step (A2), with acrylic acid being removed from this acrylic acid phase and at least part of the depleted acrylic acid phase being fed to step (A2). Here, it is preferred that the part of the depleted acrylic acid phase is, before being fed in, subjected to a combustion, preferably a gas-phase combustion and particularly preferably a catalytic gas-phase combustion, as described in WO-A-03/051809. A depleted acrylic acid phase preferably comprises less than 5% by weight, more preferably less than 1% by weight and even more preferably less than 0.1% by weight, in each case based on the depleted acrylic acid phase, of acrylic acid. Further constituents of the depleted acrylic acid phase are water, nitrogen and $CO_2$. The part of the depleted acrylic acid phase can, in particular after combustion, advantageously be used as entrainer gas in the process of the invention for preparing acrylic acid. Furthermore, the stream of oxygen or air required for oxidation of the acrolein can either be simultaneously used as entrainer gas in step (a) or be fed directly into step (A2) for the purpose of oxidation to form acrylic acid.

The invention further provides an apparatus for preparing acrolein, which comprises, connected in a fluid-conducting manner,
  a reactor for converting glycerol in an aqueous glycerol phase into acrolein,
  means of feeding an aqueous glycerol phase to the reactor,
  a distillation unit for the removal of acrolein,
  separation means for separating off the depleted acrolein phase,
  purification means for purifying the depleted acrolein phase and
  a return line which connects the separation means, the purification means and the reactor in a fluid-conducting manner.

In a particular embodiment of the apparatus of the invention for preparing acrolein, the reactor for converting glycerol into acrolein comprises a dehydration catalyst. This dehydration catalyst is preferably arranged in a fixed manner in the reactor.

This can be achieved, firstly, by the dehydration catalyst being immobilized on walls of the reactor or, if the dehydration catalyst is present in the form of particles or is immobilized thereon, by means of suitable sieves and filters being present in the reactor to prevent flushing-out of these particles.

The reactor is preferably followed by a neutralization unit from which alkali is fed in before the acrolein reaction phase is distilled.

In further embodiments of the apparatus of the invention for preparing acrolein, the purification means are selected from among a filtration unit, means for reverse osmosis, an electrodialysis unit, an ion-exchange unit and a combination of at least two thereof.

The filtration unit serves, in particular, to discharge high boilers and preferably comprises at least one microfilter, ultrafilter, a nanofilter or a combination of at least two thereof, with the nanofilter preferably being a membrane.

In a preferred embodiment of the apparatus of the invention for preparing acrolein, the purification means therefore comprises a nanofilter, with this nanofilter preferably comprising a polymeric nanofiltration membrane which is in turn preferably made of a polyamide or a polyether sulfone. As polymeric nanofiltration membranes, preference is given to polymeric nanofiltration membranes which have been mentioned at the outset as preferred polymeric nanofiltration membranes in connection with the process of the invention for preparing acrolein.

Furthermore, preference is also given, in connection with the apparatus of the invention for preparing acrolein, to the nanofilter being made of a wound module comprising the polymeric nanofiltration membrane and the wound module having a feed spacer of at least 40 mm. In this context, reference is likewise made to the relevant statements about preferred wound modules in respect of the process of the invention for preparing acrolein.

In a preferred embodiment of the apparatus of the invention for preparing acrolein, the filtration unit has an upstream filter for separating off solid constituents, followed by a nanofiltration filter and/or means for reverse osmosis.

In a further preferred embodiment of the apparatus of the invention for preparing acrolein, the purification means contain a filtration unit and/or means for reverse osmosis and a, preferably downstream, electrodialysis unit. This can be followed by means for nanofiltration and/or reverse osmosis and/or ion-exchange treatment. In a preferred embodiment, an ion-exchange unit downstream of the electrodialysis unit is present.

The apparatus of the invention preferably contains means for purifying the aqueous glycerol phase before the first introduction into the reactor. The means for purification are preferably selected from among a filtration unit, a distillation unit, means for reverse osmosis, an electrodialysis unit and an ion-exchange unit.

In addition, means for taking off the depleted acrolein phase after the purification by means of the purification unit can be present.

In a further preferred embodiment, the apparatus of the invention for preparing acrolein comprises a reactor for producing glycerol from glycerides.

The invention also provides an apparatus for preparing acrylic acid having the features of the apparatus of the invention for preparing acrolein and additionally comprising an oxidation reactor for the oxidation of acrolein to acrylic acid, with the apparatus for preparing acrolein being connected to the oxidation reactor in a fluid-conducting manner.

In one embodiment, the oxidation reactor comprises a multioxide catalyst as powder, layer or a pellet or a combination of at least two thereof. These powders, layers or pellets can be located on metal walls of metal plates or metal tubes. In the apparatus of the invention for preparing acrylic acid, preference is given to plate reactors, for example ones having heat transfer sheets, or reactors having a plurality of tubes, also referred to as shell-and-tube reactors, with shell-and-tube reactors being particularly preferred. As regards the composition of the multioxide catalysts, the information in WO-A-03/051809 is hereby incorporated by reference into the present disclosure, with particular preference being given to catalysts based on molybdenum, vanadium and tungsten. The oxidation reactor is preferably followed by a work-up unit. In this context, preference is given to the work-up unit comprising a quenching unit. Preference is also given to the apparatus of the invention for preparing acrylic acid comprising a water removal unit which is preferably combined with the quenching unit and contributes in an advantageous way to production of the acrylic acid phase depleted in acrylic acid, with the disclosure of WO-A-03/051809 also being incorporated by reference in this context.

The apparatus of the invention for preparing acrylic acid develops, for example, the apparatuses disclosed in WO-A-2006/092272 and DE-A-10 2005 028 624, without being restricted to the embodiments disclosed there, further in an inventive way, essentially in respect of the configuration of the process as a circuit, the purification of the depleted acrolein reaction phase, the purification of the crude glycerol fed in and the possibility of feeding glycerol into the circuit. The apparatuses disclosed in WO-A-2006/092272 and DE-A-10 2005 028 624 and the features thereof are hereby expressly incorporated by reference, especially FIGS. 1 to 5 of WO-A-2006/092272 and the relevant explanations in the description and also FIG. 1 of DE-A-10 2005 028 624 and the corresponding explanations in the description in paragraph [0061].

The apparatus of the invention for preparing acrylic acid is, in a preferred embodiment, characterized by the following features connected with one another in a fluid-conducting manner:

a dehydration unit;
a gas-phase oxidation unit downstream thereof;
where the dehydration unit has
a starting material feed facility;
an acrolein reaction region downstream thereof;
a pressure regulator downstream thereof; and
a depletion unit downstream thereof, with the depletion unit being connected to the gas-phase oxidation unit in a fluid-conducting manner;
and purification means (5) according to the invention and a return line (6);
where the gas-phase oxidation unit has, downstream of the depletion unit,
a reactor comprising a multioxide catalyst; and
a work-up unit.

The means for feeding in the aqueous glycerol phase (starting material feed facility) is, in one embodiment, achieved by taking the starting material from a tank which can accommodate either glycerol as such or glycerol in the form of an aqueous solution. As regards the acrolein reaction region, reference is firstly made to what has been said above. In addition, the acrolein reaction region preferably has a diameter which is longer than the cross section in the region in which it has a tubular configuration.

The pressure regulator located downstream of the acrolein reaction region viewed from the starting material feed facility and in the sense of the flow of the reactants and reaction products is preferably at least one, optionally two or more, pressure regulators which are preferably configured as pressure regulating valve, for example as relief valve. This is in turn followed downstream by a depletion unit. In a preferred configuration of the apparatus of the invention, the depletion unit can directly follow the pressure regulator. This is particularly preferred when the removal of acrolein from the acrolein reaction phase present upstream of the pressure regulator is effected by depressurization of the acrolein reaction phase. These measures reduce or completely prevent further reaction of the acrolein phase and thus also the formation of undesirable secondary components.

In another embodiment of the apparatus of the invention, the depletion unit can have a heat exchanger. This is preferably provided at the beginning of the depletion unit. In another embodiment of the apparatus of the invention, the heat exchanger is followed by a separation apparatus which is configured as a membrane or crystallizer and in particular as a distillation column. It is also advantageous for a heating element to be provided in the apparatus of the invention either in the acrolein reaction region or upstream of the acrolein reaction region or in both places. This heating element is preferably thermally coupled with the heat exchanger provided in the depletion unit.

The invention further provides an apparatus for preparing water-absorbing polymer structures having the features of the apparatus of the invention for preparing acrylic acid and additionally containing a polymerization reactor, wherein the apparatus for preparing acrylic acid is connected in a fluid-conducting manner to the polymerization reactor, preferably with insertion of the work-up unit.

The invention also provides a process for synthesizing glycerol, acrolein, acrylic acid or water-absorbing polymer structures using an apparatus according to the invention.

The invention further provides the preparation of water-absorbing polymer structures by polymerization of acrylic acid. Here, the invention provides, in a preferred embodiment, a process for preparing polymers, in particular water-absorbing polymer structures, by free-radical polymerization of acrylic acid, which comprises at least the steps:

i) provision of an optionally partially neutralized acrylic acid and a monomer phase comprising a crosslinker, with the acrylic acid being obtained by the above-described process;
ii) free-radical polymerization of the monomer phase to give a hydrogel;
iii) optionally comminution of the hydrogel;
iv) drying of the hydrogel to give a particulate water-absorbing polymer structure;
v) optionally milling of the particulate water-absorbing polymer structure;
vi) surface-modification of the particulate water-absorbing polymer structure.

This free-radical polymerization is preferably carried out in the presence of crosslinkers and also using acrylic acid in at least partially neutralized form, so that crosslinked, water-absorbing polymer structures are obtained in this way. As regards the details of the preparation of such water-absorbing polymer structures based on acrylic acid, reference may be made to "*Modern Superabsorbent Polymer Technology*", F. L. Buchholz and A. T. Graham, Wiley-VCH-Verlag. The disclosure of this textbook in respect of the details for the preparation of superabsorbents based on crosslinked polyacrylates is hereby incorporated by reference into the disclosure of the present invention.

Furthermore, preference is given according to the invention to the acrylic acid in process step i) being present as salt to an extent of at least 20 mol %, particularly preferably at least 50 mol %, based on the monomer.

A contribution to achievement of the objects mentioned at the outset is also provided by the water-absorbing polymer structures which can be obtained by the above-described process.

A contribution to achieving the objects mentioned at the outset is also provided by water-absorbing polymer structures which are based to an extent of at least 25% by weight, preferably at least 50% by weight, even more preferably at least 75% by weight and most preferably at least 95% by weight, of acrylic acid, where at least 80% by weight, preferably at least 90% by weight and most preferably at least 95% by weight, of the acrylic acid monomers used for preparing the water-absorbing polymer structures have been obtained by the above-described process from glycerol via acrolein as intermediate and have been coated with from 0.01 to 10% by weight, based on the weight of the water-absorbing polymer structures, of a coating agent, with preferred coating agents being the coating agents which have been mentioned above in connection with the process of the invention for preparing water-absorbing polymer structures. The coating agent is preferably not a surface after-crosslinker.

In a particular embodiment of the water-absorbing polymer structures of the invention, these are based to an extent of at least 25% by weight, preferably at least 35% by weight and most preferably at least 45% by weight, on natural, biodegradable polymers, preferably on carbohydrates such as cellulose or starch.

A contribution to achieving the objects mentioned at the outset is also provided by hygiene articles comprising the above-described, water-absorbing polymer structures or a water-absorbing polymer structure which can be obtained by the process of the invention.

A contribution to achieving the objects mentioned at the outset is also provided by the use of acrolein which can be obtained by the process of the invention for preparing acrolein or of acrylic acid which can be obtained by the process of the invention for preparing acrylic acid or of both monomers as basis of or in fibers, films, molding compositions, textile and leather auxiliaries, flocculants, coatings, paints and varnishes, foams, films, cables, sealing materials, liquid-absorbing hygiene articles, in particular diapers and sanitary napkins, supports for plant or fungal growth regulating agents or crop protection agents, additives for building materials, packaging materials or soil additives.

A contribution to achieving the objects mentioned at the outset is also provided by fibers, films, molding compositions, textile and leather auxiliaries, flocculants, coatings, paints and varnishes, foams, films, cables, sealing materials, liquid-absorbing hygiene articles, in particular diapers and sanitary napkins, supports for plant or fungal growth regulating agents or crop protection agents, additives for building materials, packaging materials or soil additives comprising or based on acrolein which can be obtained by the process for preparing acrolein or on acrylic acid which can be obtained by the process of the invention for preparing acrylic acid.

Furthermore, a contribution to achieving the objects mentioned at the outset is provided by a process for purifying a glycerol phase G4 comprising glycerol, water and residual materials other than glycerol and water, where the glycerol phase G4 has a glycerol content in the range from 20 to 80% by weight, but preferably at least 30% by weight, even more preferably at least 40% by weight and still more preferably at least 50% by weight, in each case based on the total weight of the glycerol phase G4, and the glycerol phase G4 is subjected to a nanofiltration to give a purified glycerol phase G5.

The glycerol phase G4 is preferably a crude glycerol phase as has been described above in connection with the process of the invention for preparing acrolein. At least one accompanying salt is therefore at least partly removed from this crude glycerol phase by nanofiltration.

In this context, preference is also given to the nanofiltration being carried out by means of a polymeric nanofiltration membrane which is preferably present in a wound module. As polymeric nanofiltration membranes and wound modules, preference is once again given to the polymeric nanofiltration membranes and wound modules which have been mentioned above in connection with the process of the invention for preparing acrolein.

Furthermore, preference is given in connection with the process of the invention to purifying a glycerol phase G4 by carrying out the purification under the pressure and temperature conditions which have been mentioned above as preferred pressure and temperature conditions in connection with the process of the invention for preparing acrolein, there in connection with the purification of the glycerol phase G2 or the mixed phase M1 by means of nanofiltration.

Also in connection with the process of the invention for purifying a glycerol phase G4, the permeate yield is preferably at least 90% by weight, particularly preferably at least 95% by weight and most preferably at least 99% by weight.

In a particular variant of the process of the invention for purifying a glycerol phase G4 comprising glycerol, water and residual materials other than glycerol and water, the nanofiltration is followed by treatment of the permeate with activated carbon.

A contribution to achieving the objects mentioned at the outset is also provided by the use of a purified glycerol phase G5 obtained by the process of the invention for purifying a glycerol phase G4, or as glycerol phase G3 in the process of the invention for preparing acrolein.

The present invention is illustrated by nonlimiting drawings. FIGS. 1 to 9 schematically show illustrative embodiments of the present invention.

FIG. 1 schematically shows an illustrative apparatus 1 according to the invention. Here, the conversion of glycerol into acrolein takes place in a reactor (1). An aqueous glycerol phase is fed to the reactor via means (2). The acrolein reaction phase is fed to a distillation unit (3). Here, it preferably passes through a neutralization unit (20) by means of which the alkali is fed in. The acrolein is taken off after the distillation and can be processed further in an oxidation reactor (10) to give acrylic acid. The acrylic acid can be processed further in a polymerization reactor (11), for example to give water-absorbing polymers. The depleted acrolein reaction phase is taken off from the distillation unit (3) via removal means (4). The removal means (4) can contain a filter or a filtration unit.

The depleted acrolein reaction phase is fed to the purification means (5). After purification, the purified solution is fed back to the reactor (1) via a return line (6).

In a preferred embodiment of the invention, means for feeding in crude glycerol (2) can be available. In a further preferred embodiment of the invention, the aqueous glycerol phase originally fed to the reactor is taken from a reactor (9) for producing glycerol from glycerides. In a further embodiment of the invention, the glycerol fed in is purified in purification means (7) before being introduced into the reactor (1).

Figure 2:
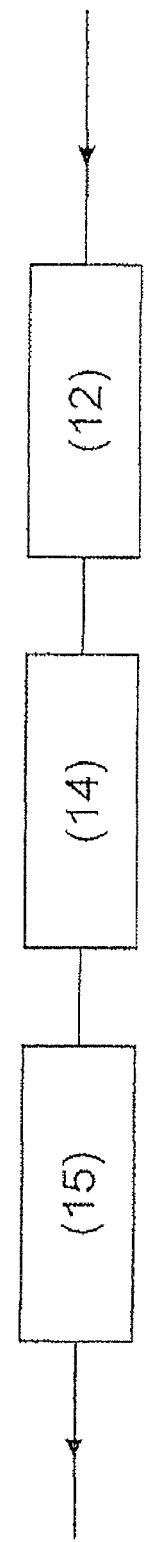
FIG. 2 is a schematic of an aspect of an embodiment of an apparatus in accordance with the current invention.

FIG. 2 corresponds to process alternative ii) of the process of the invention for preparing acrolein and shows a preferred configuration of the purification means (5) for purifying the acrolein reaction phase. Here, the depleted acrolein reaction phase is purified by means of a filter unit (12) followed by an electrodialysis unit (14) followed by an ion-exchange unit (15). In this embodiment, the filter unit (12) preferably comprises a prefilter in combination with a nanofilter or means for reverse osmosis, preferably a nanofilter.

Figure 3:
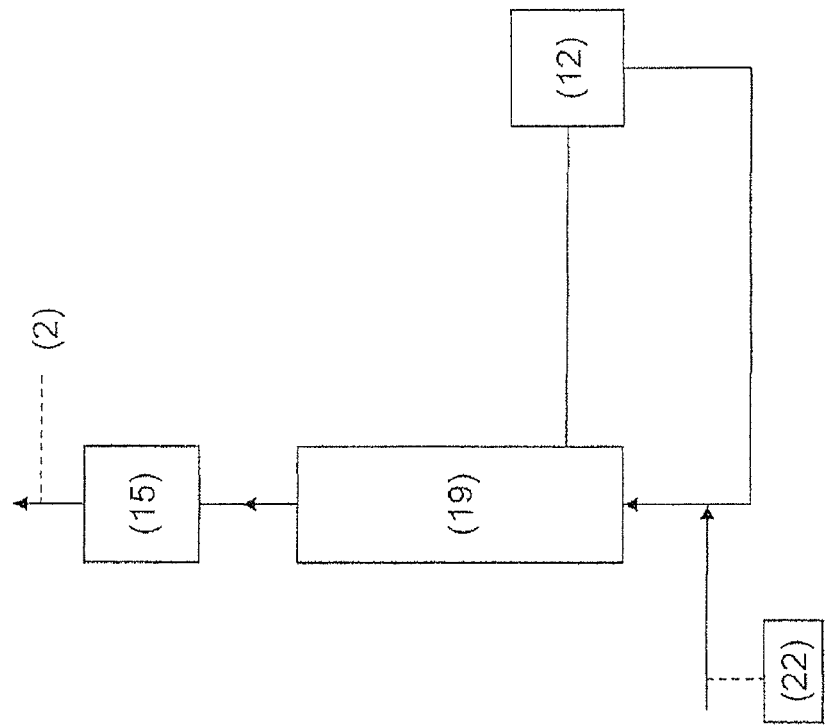
FIG. 3 is a schematic of a further aspect of an embodiment of an apparatus in accordance with the current invention.

FIG. 3 corresponds to process alternative i) of the process of the invention for preparing acrolein and shows a preferred configuration of the means (7) for purifying the glycerol phase before introduction into the reactor (1). Here, crude glycerol is fed into a distillation unit (19). The glycerol which has been purified by distillation is fed to an ion-exchange unit (15). The glycerol which has been purified in this way is fed to the reactor (1). The distillation residue is freed of high boilers and salts in a filtration unit (12). The filtration unit (12) comprises a prefilter connected to a nanofilter and/or a reverse osmosis unit. The distillation residue which has been purified in this way is fed back to the distillation in a circulation process.

Figure 4:
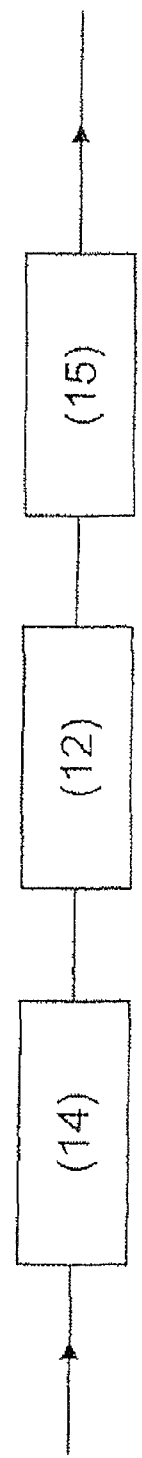
FIG. 4 is a schematic of a further aspect of an embodiment of an apparatus in accordance with the current invention.

FIG. 4 corresponds to process alternative i) of the process of the invention for preparing acrolein and shows a further preferred configuration of the means (7) for purifying the glycerol phase before introduction into the reactor (1). The crude glycerol is firstly purified by means of an electrodialysis unit (14) which can contain a prefilter. Further purification is subsequently effected by means of a filtration unit (12) containing a prefilter and a nanofilter and/or means for reverse osmosis, preferably a nanofilter. The solution is subsequently purified in an ion-exchange unit (15).

Figure 5:
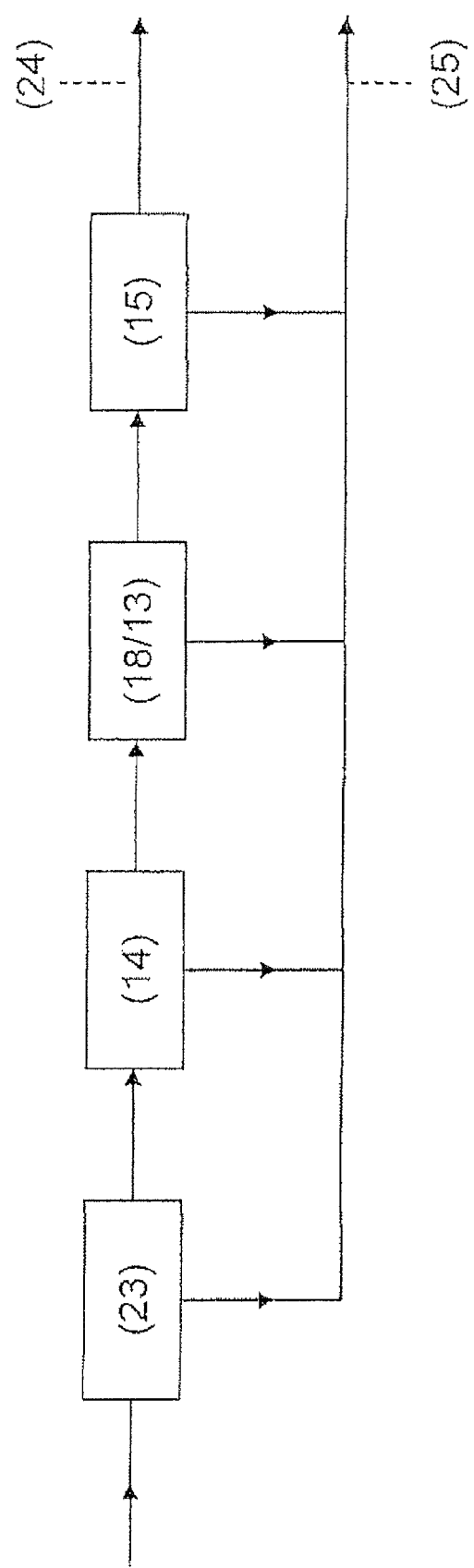
FIG. 5 is a schematic of a further aspect of an embodiment of an apparatus in accordance with the current invention.

FIG. 5 shows a preferred embodiment of purification means (5) or (7) according to the invention, which are suitable both for purifying the acrolein reaction phase and for purifying the crude glycerol initially fed in (and thus suitable for realizing both process alternative i) and process alternative ii) of the process of the invention for preparing acrolein). Here, the glycerol solution to be purified is firstly filtered by means of a filter (23), then fed to an electrodialysis unit (14), then treated using a nanofilter (18) and/or means for reverse osmosis (13), preferably a nanofilter (18), and subsequently fed to an ion-exchange unit (15). The purified glycerol solution is taken off via a line (24). The by-products such as salts, solids and further components are discharged via a line (25).

Figure 6:
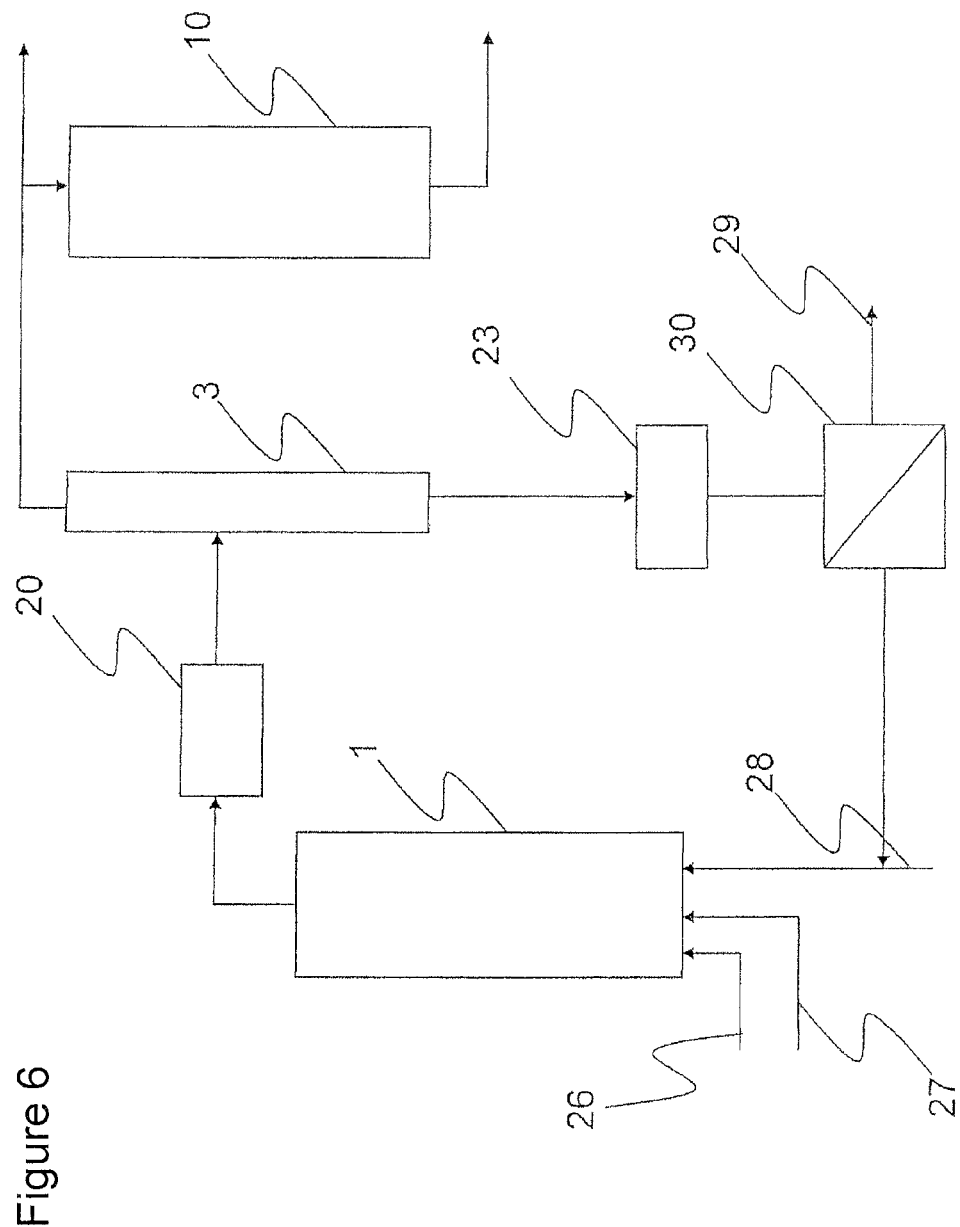
FIG. 6 is a schematic of a further aspect of an embodiment of an apparatus in accordance with the current invention.

FIG. 6 shows a reactor for converting glycerol into acrolein (1), into which an inert gas feed facility (26), in which usually nitrogen is fed into the reactor for the reaction of glycerol (1), and a catalyst feed facility (27), in which usually liquid catalyst is fed into the reactor for converting glycerol into acrolein (1), open. The reactor for converting glycerol into acrolein (1) is followed by a neutralization unit (20) connected via a line to the reactor (1), and this neutralization unit is in turn connected via a line to a distillation unit (3). A line leading from the top of the distillation unit (3) connects the distillation unit firstly to an oxidation reactor for the oxidation of acrylic acid (10). Secondly, this line divides and releases gaseous constituents coming from the distillation unit (3) into the surroundings. From the oxidation reactor for the oxidation of acrylic acid (10), the acrylic acid is conveyed via a further line to further uses, for example a polymerization reactor (11) (not shown here). In the lower region of the distillation unit (3), a line leads to a filter (23) which is followed by a separator (30) for discharging high boilers and salts. This separator (30) can be configured as a nanofiltration or optionally as a reverse osmosis, preferably as a nanofiltration. These high boilers and salts are taken from the circuit by means of a high boiler discharge line (29). The separator (30) is in turn connected to a feed facility for technical-grade glycerol (28) which opens into the reactor for converting glycerol into acrolein (1). The process variant ii), in particular, of the process of the invention for preparing acrolein can be realized by means of the apparatus depicted in FIG. 6.

Figure 7:
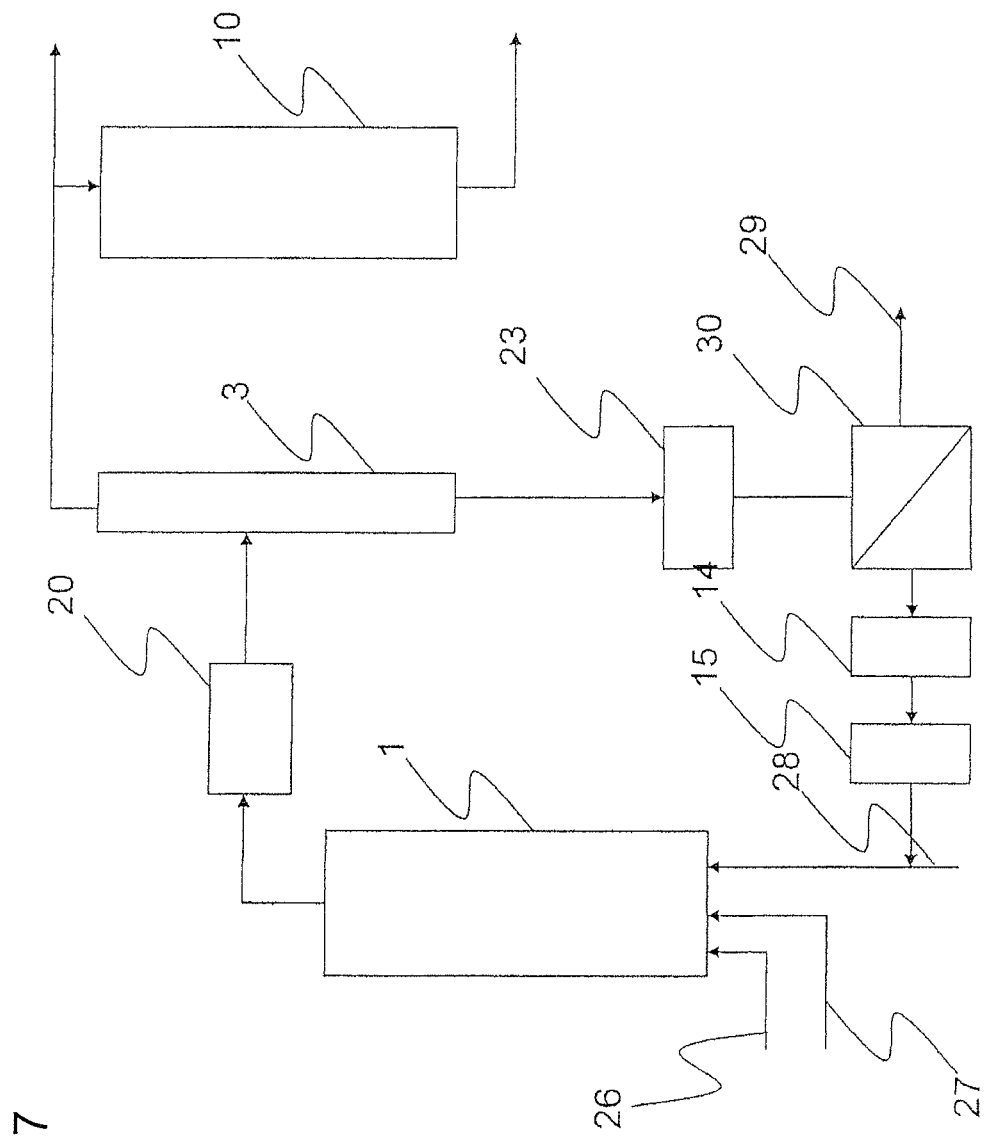
FIG. 7 is a schematic of a further aspect of an embodiment of an apparatus in accordance with the current invention.

In FIG. 7, an electrodialysis unit (14) which is connected to an ion-exchange unit (15) which is in turn connected to the feed facility for technical-grade glycerol (28) is provided between the separator (30) and the feed facility for technical-grade glycerol downstream of the separator (30) in addition to the embodiment according to the invention depicted in FIG. 6. The process variant ii), in particular, of the process of the invention for preparing acrolein can also be realized by means of the apparatus depicted in FIG. 7.

Figure 8:
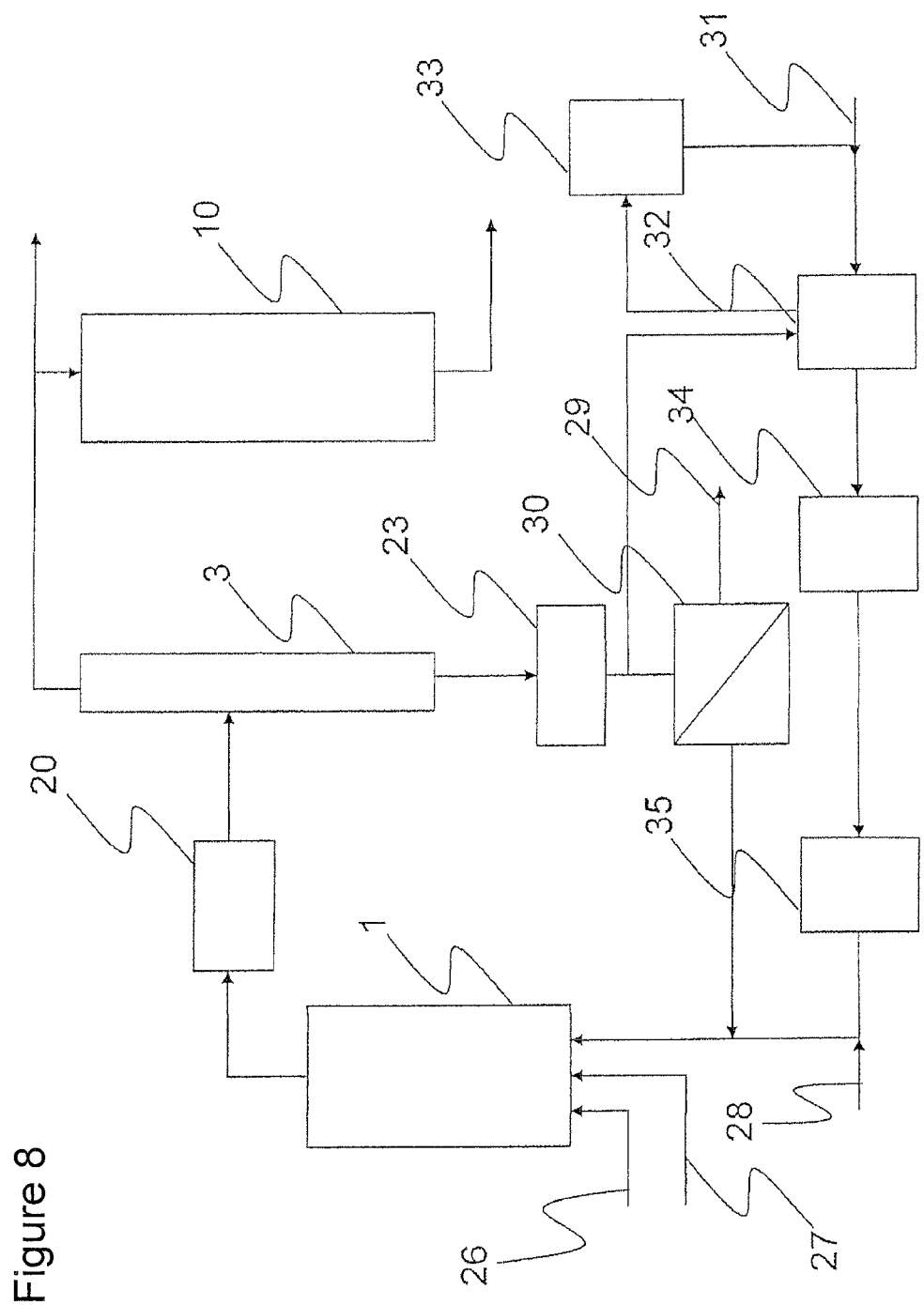
FIG. 8 is a schematic of a further aspect of an embodiment of an apparatus in accordance with the current invention.

In FIG. 8, the embodiment according to the invention depicted in FIG. 6 has been supplemented by salt-containing glycerol being fed via a crude glycerol feed line (31) into a crude glycerol still (32) into which at least part of the stream leaving the filter (23) is likewise fed. The bottom product obtained in the crude glycerol still (32) is at least partly conveyed via a salt separator (33), and the glycerol which has been at least partly freed of salt is, after leaving the salt separator (33), fed back into the crude glycerol still (32) which is followed by a glycerol still (34). Here, preference is given to the conditions, in particular pressure or temperature or both, being different in the crude glycerol still (32) and the glycerol still (34). The glycerol still (34) is followed by a crude glycerol ion exchanger (35) from which the glycerol which has been purified in this way is fed to the reactor for converting glycerol into acrolein. Both the process variant i) and the process variant ii) of the process of the invention for preparing acrolein can be realized by means of the apparatus depicted in FIG. 8.

Figure 9:
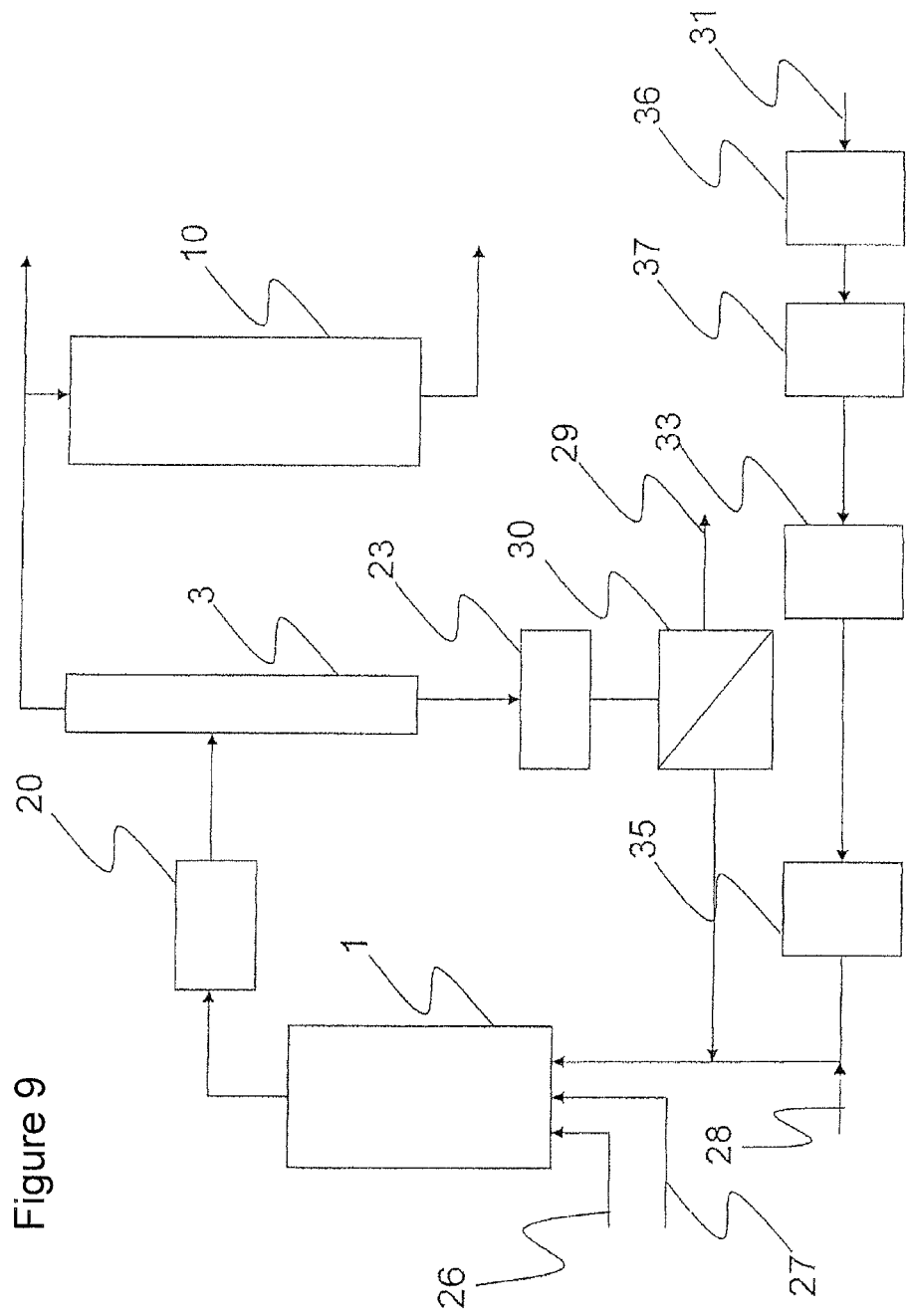
FIG. 9 is a schematic of a further aspect of an embodiment of an apparatus in accordance with the current invention.

FIG. 9 shows a supplementation of the embodiment according to the invention depicted in FIG. 6 in that crude glycerol comprising salt is fed through a crude glycerol feed line (31) via a crude glycerol filter (36) into a crude glycerol reverse osmosis (37) which is followed by a salt separator (33) which opens into a crude glycerol ion exchanger (35) which is in turn connected to the feed facility for technical-grade glycerol. Once again, both the process variant i) and the process variant ii) of the process of the invention for preparing acrolein can be realized by means of the apparatus depicted in FIG. 9.

LIST OF REFERENCE NUMERALS

1 Reactor for converting glycerol into acrolein
2 Means of feeding an aqueous glycerol phase into the reactor
3 Distillation unit
4 Removal means
5 Purification means for purifying the acrolein reaction phase
6 Return line
7 Means for purifying the glycerol phase before introduction into the reactor
8 Means for taking off the depleted glycerol phase
9 Reactor for producing glycerol from glycerides
10 Oxidation reactor for the oxidation of acrylic acid
11 Polymerization reactor
12 Filtration unit
13 Means for reverse osmosis
14 Electrodialysis unit
15 Ion-exchange unit
16 Microfilter
17 Ultrafilter
18 Nanofilter
19 Distillation unit
20 Neutralization unit
21 Feed line for reaction constituents
22 Means for feeding in crude glycerol
23 Filter
24 Discharge line for the glycerol solution
25 Discharge line for the salts, solids, by-products
26 Feed line for inert gas
27 Feed line for catalyst
28 Feed line for technical-grade glycerol
29 High boiler discharge
30 Separator
31 Crude glycerol feed facility
32 Crude glycerol still
33 Salt separator
34 Glycerol still
35 Crude glycerol ion exchanger
36 Crude glycerol filter
37 Crude glycerol reverse osmosis

The invention claimed is:

1. A process for preparing acrolein, which comprises the following steps:
   (a) dehydration of an aqueous glycerol phase G1 in an acrolein reaction region to give an aqueous acrolein reaction phase wherein the aqueous acrolein reaction phase comprises a liquid solvent selected from hydroxypiperidine, sulfolane, diglyme, tetraglyme, dioxane, trioxane or γ-butyrolactone, and wherein the acrolein reaction region is constructed with a first metal and the acrolein reaction region further comprises a different metal or metal compound which is immobilized in particulate form by means of sieves or filters present in the acrolein reaction region;
   (b) at least partial separation of the aqueous acrolein reaction phase into an acrolein-rich acrolein phase and a residue phase R1;
   wherein said residue phase R1 is low in acrolein compared to the acrolein phase, and wherein the residue phase R1 comprises glycerol, water and residual materials other than glycerol and water; and
   (c) recirculation of at least part of the residue phase R1 to step (a);
   wherein
   i) at least one of the residual materials present in a glycerol phase G2 comprising glycerol, water and residual materials other than glycerol and water is separated from the glycerol phase G2 and the purified glycerol phase G2 obtained in this way is fed directly to the acrolein reaction region or
   ii) at least one of the residual materials other than glycerol and water is separated off from a mixed phase M1 obtained by mixing said glycerol phase G2 comprising glycerol, water and residual materials other than glycerol and water with said low-acrolein residue phase R1 and the purified mixed phase M1 obtained in this way is fed to the acrolein reaction region,
   wherein a further glycerol phase G3 is fed in addition to the purified glycerol phase G2 or the purified mixed phase M1 into the acrolein reaction region, wherein the glycerol phase G3 is obtained as distillate in the distillation of crude glycerol obtained in the cleavage or transesterification of triglycerides, and wherein at least part of a bottom product obtained in the distillation of the crude glycerol goes through a salt separator and is subsequently fed back into the distillation of the crude glycerol.

2. The process as claimed in claim 1, wherein the glycerol phases G3 and G2 differ in terms of their glycerol content or salt content or their content of organic compounds other than glycerol or at least two of these contents.

3. The process as claimed in claim 1, wherein the glycerol phase G2 is a crude glycerol phase obtained as a reaction product in the cleavage or transesterification of triglycerides.

4. The process as claimed in claim 1, wherein the step (c) i) or ii) is carried out by means of at least one of the following methods of separation:
   α1 distillation;
   α2 filtration;
   α3 electrodialysis;
   α4 ion-exchange treatment.

5. The process as claimed in claim 1, wherein the separation according to the alternative i) or ii) is carried out by means of a polymeric nanofiltration membrane.

6. The process as claimed in claim 1, wherein the separation according to alternative i) or ii) is carried out by means of a filtration followed by an electrodialysis.

7. The process as claimed in claim 1, wherein the acrolein reaction region comprises a dehydration catalyst.

8. The process as claimed in claim 1, wherein the acrolein reaction phase before process step (b) is under a higher pressure than during process step (b).

9. The process as claimed in claim 1, further comprising supplying an entrainer gas to the acrolein reaction region.

10. The process as claimed in claim 1, wherein the different metal or metal compound is a metal compound comprising a heteropolyacid.

11. The process as claimed in claim 10, wherein the heteropolyacid is selected from phosphotungstic acids, silicotungstic acids, silicomolybdic acids, or vanadium compound acids.

* * * * *